United States Patent
Weisshaupt et al.

(10) Patent No.: US 10,772,679 B2
(45) Date of Patent: *Sep. 15, 2020

(54) SURGICAL SYSTEM FOR CONNECTING BODY TISSUE

(71) Applicant: Aesculap AG, Tuttlingen (DE)

(72) Inventors: Dieter Weisshaupt, Immendingen (DE);
Anton Keller, Duerbheim (DE);
Christoph Rothweiler, Donaueschingen (DE)

(73) Assignee: Aesculap AG, Tuttlingen (DE)

( * ) Notice: Subject to any disclaimer, the term of this patent is extended or adjusted under 35 U.S.C. 154(b) by 385 days.

This patent is subject to a terminal disclaimer.

(21) Appl. No.: 15/345,622

(22) Filed: Nov. 8, 2016

(65) Prior Publication Data

US 2017/0071666 A1 Mar. 16, 2017

Related U.S. Application Data

(63) Continuation of application No. 12/968,942, filed on Dec. 15, 2010, now Pat. No. 9,492,172.

(30) Foreign Application Priority Data

Dec. 17, 2009 (DE) ........................ 10 2009 059 196

(51) Int. Cl.
*A61B 18/14* (2006.01)
*A61B 17/115* (2006.01)
(Continued)

(52) U.S. Cl.
CPC .......... *A61B 18/1492* (2013.01); *A61B 17/11* (2013.01); *A61B 17/115* (2013.01);
(Continued)

(58) Field of Classification Search
CPC ... A61B 17/11; A61B 17/115; A61B 17/1155; A61B 2017/07214; A61B 18/1442; A61B 18/1492; A61B 2018/00214
See application file for complete search history.

(56) References Cited

U.S. PATENT DOCUMENTS 5,403,312 A 4/1995 Yates et al.
5,558,671 A 9/1996 Yates
(Continued)

FOREIGN PATENT DOCUMENTS

DE 69420650 5/2000
DE 69834644 5/2007
(Continued)

*Primary Examiner* — Eun Hwa Kim
(74) *Attorney, Agent, or Firm* — Lipsitz & McAllister, LLC

(57) ABSTRACT

A surgical system for connecting body tissue is provided. The surgical system includes a surgical instrument having two tool elements movable relative to each other, each of which comprises a high-frequency electrode. The high-frequency electrodes, in an approach position of the tool elements, define a minimum distance from each other, lying opposite each other and facing each other. The instrument has a shaft at the distal end of which at least a first one of the tool elements is arranged or formed. A second tool element is movable from an operating position, in which it is adapted for movement into the approach position, into a removal position and/or vice versa. A surface area of a perpendicular projection of the second tool element onto a projection plane extending perpendicularly to a shaft direction in a region of the second tool element is smaller in the removal position than in the operating position.

13 Claims, 19 Drawing Sheets

(51) Int. Cl.
*A61B 17/11* (2006.01)
*A61B 18/00* (2006.01)
*A61B 17/072* (2006.01)
*A61B 18/12* (2006.01)

(52) U.S. Cl.
CPC ....... *A61B 18/1442* (2013.01); *A61B 17/1114* (2013.01); *A61B 17/1155* (2013.01); *A61B 18/1445* (2013.01); *A61B 18/1447* (2013.01); *A61B 2017/07214* (2013.01); *A61B 2017/1125* (2013.01); *A61B 2017/1132* (2013.01); *A61B 2017/1135* (2013.01); *A61B 2017/1139* (2013.01); *A61B 2018/0063* (2013.01); *A61B 2018/00083* (2013.01); *A61B 2018/00202* (2013.01); *A61B 2018/00494* (2013.01); *A61B 2018/00607* (2013.01); *A61B 2018/00619* (2013.01); *A61B 2018/126* (2013.01); *A61B 2018/1253* (2013.01)

(56) References Cited

U.S. PATENT DOCUMENTS

| | | |
|---|---|---|
| 5,693,051 A | 12/1997 | Schulze et al. |
| 5,957,920 A | 9/1999 | Baker |
| 6,035,238 A | 3/2000 | Ingle et al. |
| 6,091,995 A | 7/2000 | Ingle et al. |
| 6,216,704 B1 | 4/2001 | Ingle et al. |
| 6,270,497 B1 | 8/2001 | Sekino et al. |
| 6,395,002 B1 | 5/2002 | Ellman et al. |
| 6,480,746 B1 | 11/2002 | Ingle et al. |
| 6,626,901 B1 | 9/2003 | Treat et al. |
| 6,699,245 B2 | 3/2004 | Dinger et al. |
| 7,025,763 B2 | 4/2006 | Karasawa et al. |
| 7,167,758 B2 | 1/2007 | Baker et al. |
| 7,168,604 B2* | 1/2007 | Milliman ............ A61B 17/1114 227/175.1 |
| 7,211,080 B2 | 5/2007 | Treat et al. |
| 7,422,138 B2 | 9/2008 | Bilotti et al. |
| 7,431,191 B2 | 10/2008 | Milliman |
| 7,588,566 B2 | 9/2009 | Treat et al. |
| 7,608,073 B2 | 10/2009 | Heinrich et al. |
| 2003/0045811 A1 | 3/2003 | Hinchliffe et al. |
| 2003/0069571 A1 | 4/2003 | Treat et al. |
| 2004/0002703 A1 | 1/2004 | Xiao et al. |
| 2005/0205639 A1 | 9/2005 | Willman |
| 2006/0064086 A1 | 3/2006 | Odom |
| 2006/0201989 A1 | 9/2006 | Ojeda |
| 2007/0175963 A1 | 8/2007 | Bilotti et al. |
| 2007/0276363 A1 | 11/2007 | Patton et al. |
| 2008/0210739 A1 | 9/2008 | Milliman et al. |
| 2008/0243121 A1* | 10/2008 | Takashino ............ A61B 18/1445 606/52 |
| 2009/0043305 A1 | 2/2009 | Brodbeck et al. |
| 2009/0048589 A1 | 2/2009 | Takashino et al. |
| 2009/0056515 A1 | 3/2009 | Viola et al. |
| 2009/0270852 A1* | 10/2009 | Takashino ............ A61B 18/085 606/27 |

FOREIGN PATENT DOCUMENTS

| | | |
|---|---|---|
| DE | 69836817 | 10/2007 |
| EP | 1815805 | 8/2007 |
| EP | 1935348 | 6/2008 |
| EP | 2030578 | 3/2009 |
| EP | 2111812 | 10/2009 |
| WO | 2005/004734 | 1/2005 |
| WO | 2006/021269 | 3/2006 |
| WO | 2009/022614 | 2/2009 |

\* cited by examiner

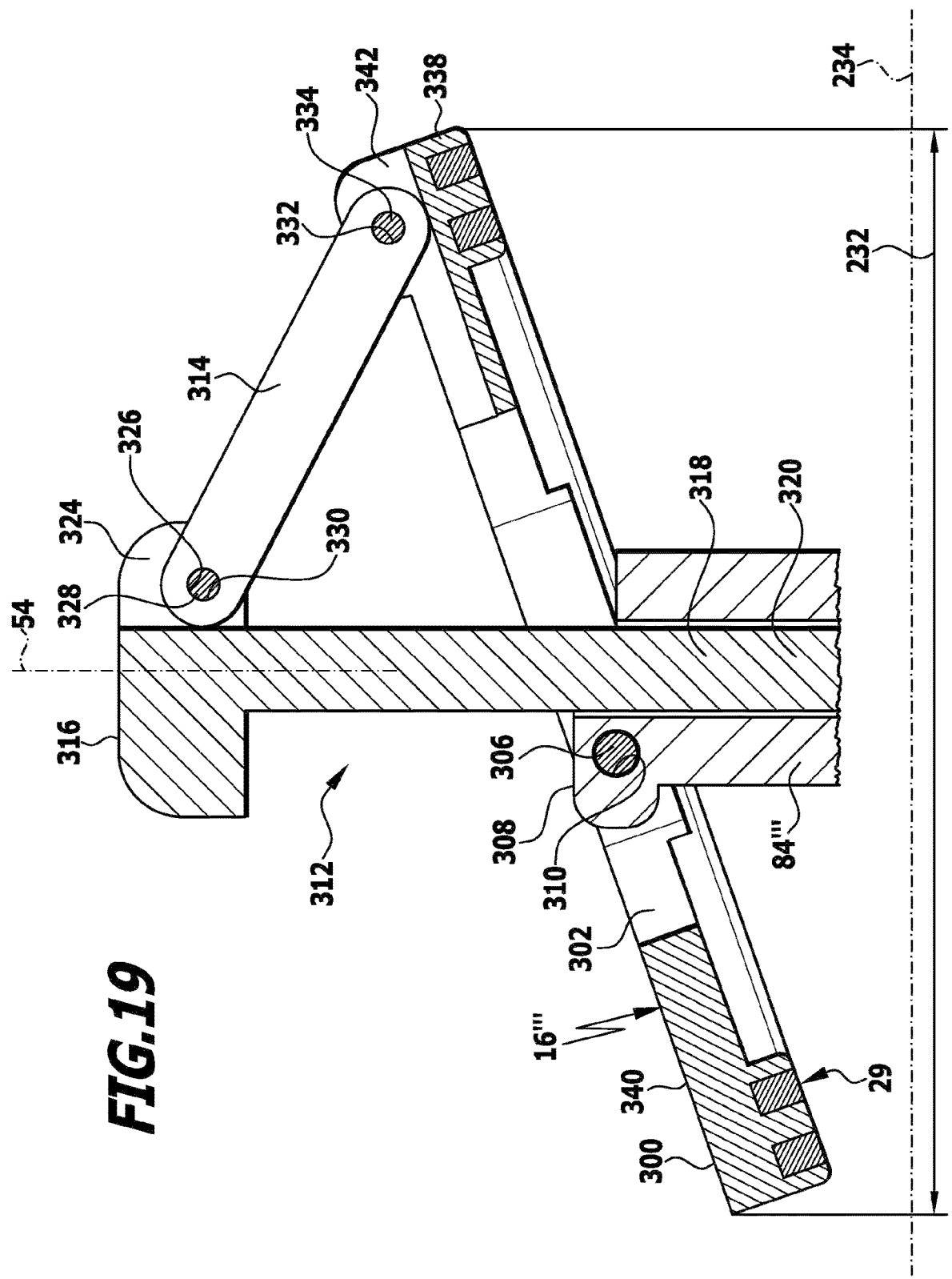

SURGICAL SYSTEM FOR CONNECTING BODY TISSUE

CROSS-REFERENCE TO RELATED APPLICATIONS

The present application is a continuation of commonly-owned co-pending U.S. patent application Ser. No. 12/968,942, filed on Dec. 15, 2010, which claims the benefit of German application number 10 2009 059 196.6 filed on Dec. 17, 2009, each of which is incorporated herein by reference in its entirety and for all purposes.

FIELD OF THE INVENTION

The present invention relates to surgical systems for connecting body tissue generally, and more specifically to a surgical system for connecting body tissue, comprising a surgical instrument having two tool elements movable relative to each other, each of which comprises a high-frequency electrode, the high-frequency electrodes, in an approach position of the tool elements, defining a minimum distance from each other, lying opposite each other and facing each other.

BACKGROUND OF THE INVENTION

Surgical systems of the kind described at the outset can be used, in particular, for connecting parts of body tissue to one another. In particular, when tubular sections of a hollow organ are connected to one another in end-to-end anastomoses, an overstretching of the tissue connection may be caused, for example, by the second tool element when the instrument is being removed through the tissue connection that has been made.

Therefore, it would be desirable to provide a surgical system which, in particular, avoids an overstretching of connections of parts of body tissue made by a flow of current when removing the surgical instrument.

SUMMARY OF THE INVENTION

In accordance with the invention a surgical system for connecting body tissue comprises a surgical instrument having two tool elements movable relative to each other. Each of the two tool elements comprises a high-frequency electrode. The high-frequency electrodes, in an approach position of the tool elements, define a minimum distance from each other, lie opposite each other and face each other. The instrument further comprises a shaft at the distal end of which at least a first one of the tool elements is arranged or formed. A second tool element is adapted to be moved from an operating position, in which it is adapted for movement into the approach position, into a removal position and/or vice versa. A surface area of a perpendicular projection of the second tool element onto a projection plane extending perpendicularly to the shaft direction in the region of the second tool element is smaller in the removal position than in the operating position

BRIEF DESCRIPTION OF THE DRAWINGS

The foregoing summary and the following description may be better understood in conjunction with the drawing figures, of which:

FIG. 19 shows a view in analogy with FIG. 18 with the second tool element partly inclined in a position as represented in FIG. 17.

DETAILED DESCRIPTION

Figure 1:
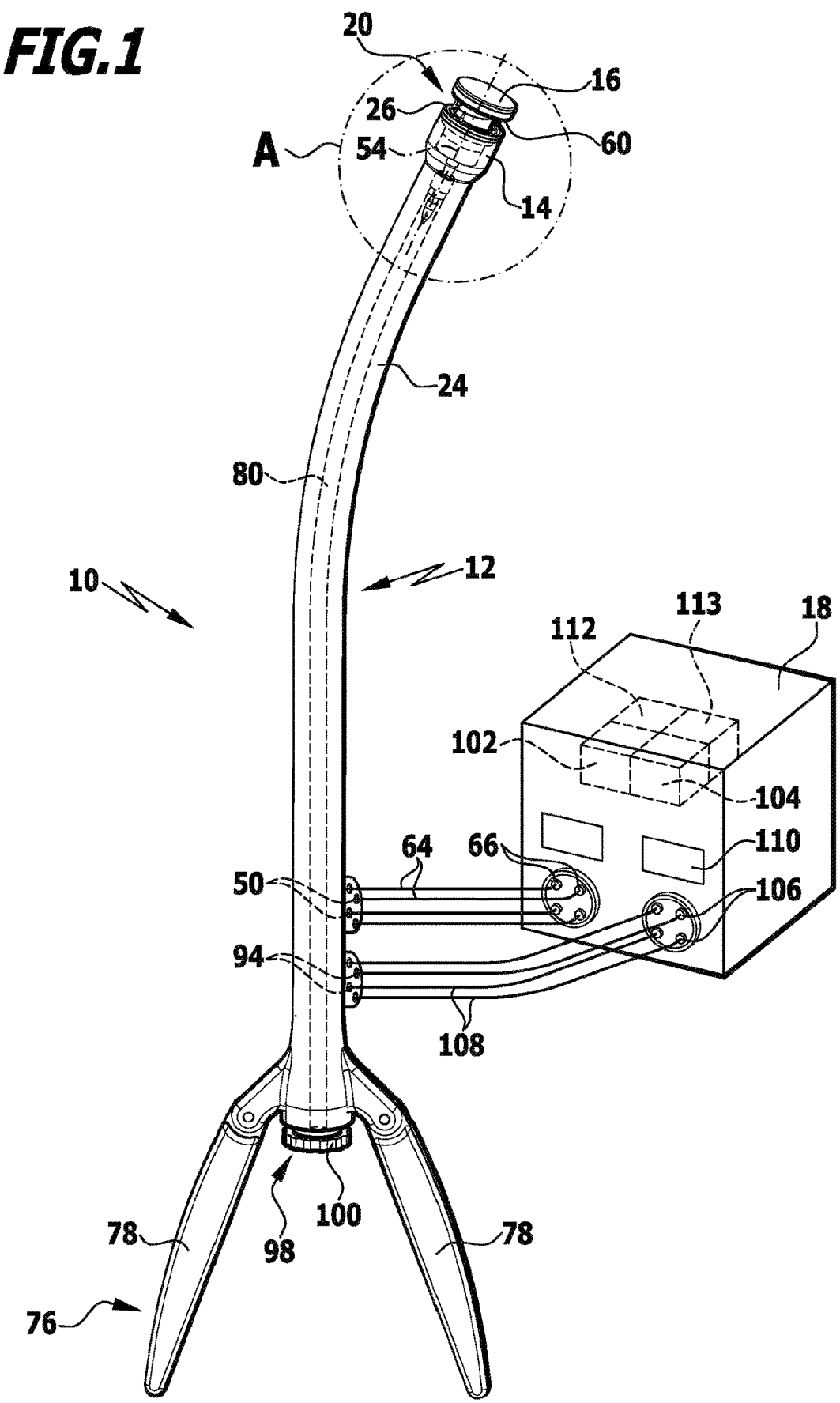
FIG. 1 shows a diagrammatic overall view of a surgical instrument for connecting parts of body tissue.
Figure 2:
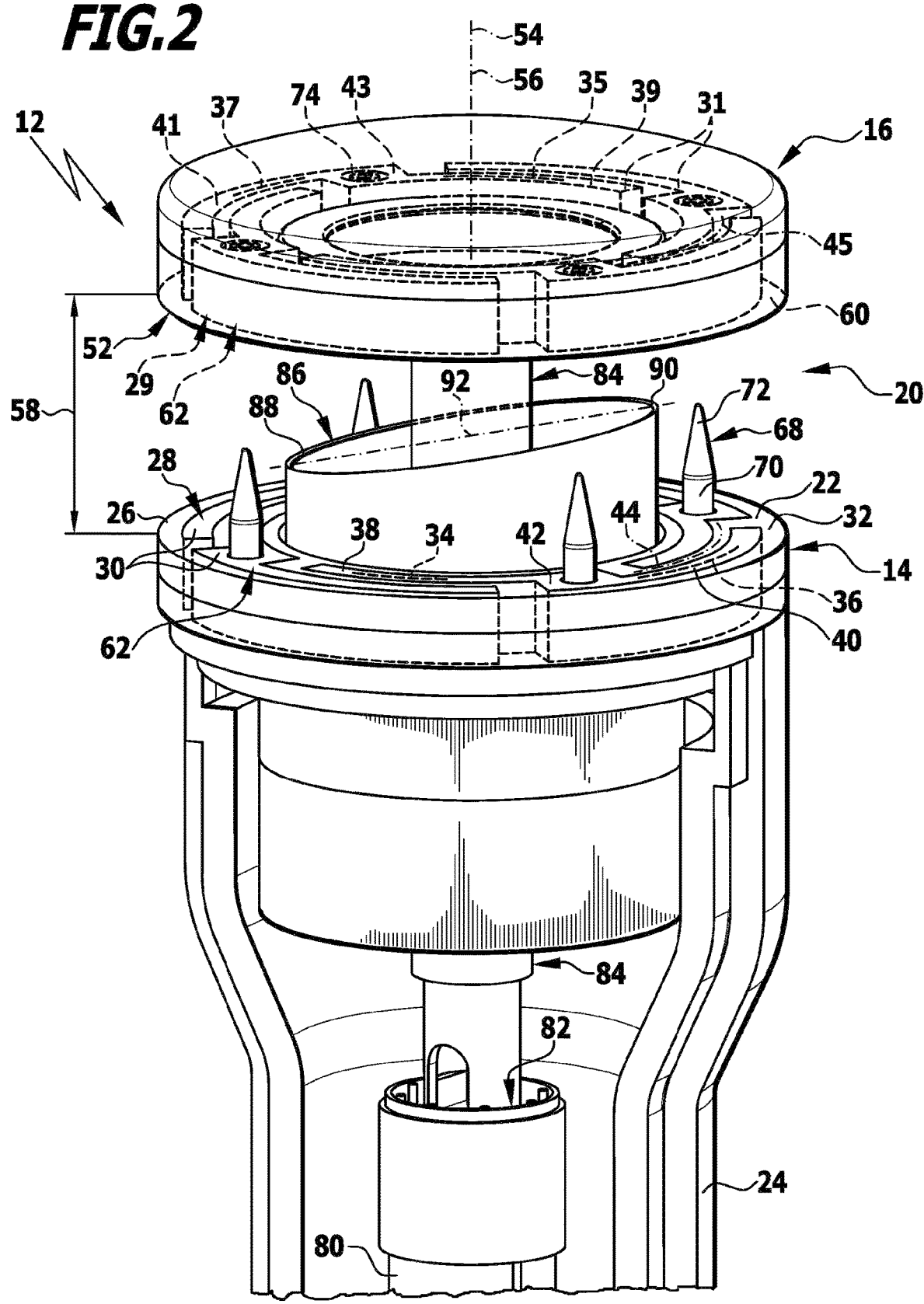
FIG. 2 shows an enlarged, perspective, partially sectional and broken-open view of area A in FIG. 1.

Although the invention is illustrated and described herein with reference to specific embodiments, the invention is not intended to be limited to the details shown. Rather, various modifications may be made in the details within the scope and range of equivalents of the claims and without departing from the invention.

The present invention relates to a surgical system for connecting body tissue, comprising a surgical instrument having two tool elements movable relative to each other, each of which comprises a high-frequency electrode, the high-frequency electrodes, in an approach position of the tool elements, defining a minimum distance from each other, lying opposite each other and facing each other, wherein the instrument comprises a shaft at the distal end of which at least a first one of the tool elements is arranged or formed, and in that a second tool element is adapted to be moved from an operating position, in which it is adapted for movement into the approach position, into a removal position and/or vice versa, a surface area of a perpendicular projection of the second tool element onto a projection plane extending perpendicularly to the shaft direction in the region of the second tool element being smaller in the removal position than in the operating position.

The advantage of being able to transfer the second tool element from the operating position to the removal position in the defined manner is, in particular, that the free surface required for passing the second tool element through the connecting site of the parts of tissue is significantly reduced in the removal position in comparison with the operating position. In particular, when the system is suitably designed, it can be ensured that in the removal position no stretching of the freshly connected parts of tissue will occur in the region of their connection when the instrument is removed from the parts of tissue connected to one another. This has a positive effect on end-to-end, side-to-end and side-to-side anastomoses. In particular, when the second tool element can be transferred from the removal position into the operating position again, several anastomoses can also be easily performed one after the other with the instrument without the instrument in its entirety having to be removed from the tubular parts of tissue to be connected to one another.

The construction of the system can be easily simplified by the second tool element being ring-shaped or plate-shaped. Furthermore, in particular, ring-shaped, i.e., self-contained electrodes can also be easily and safely arranged on such second tool elements.

To transfer the second tool element from the operating position into the removal position and/or vice versa, it is expedient for the second tool element to be mounted for movement on a holding member. For example, the second tool element can thus be moved in a defined manner relative to the holding member, and, optionally, the holding member itself relative to a further part of the instrument, for example, a shaft thereof.

Particularly simple constructions are possible for movable mountings of the second tool element on the holding member by, for example, the second tool element being mounted for displacement and/or pivotal movement on the holding member.

Expediently, the second tool element is mounted for pivotal movement about a pivot axis which extends transversely, in particular, perpendicularly, to a holding member longitudinal axis defined by the holding member. For example, a ring-shaped or plate-shaped second tool element which, in the operating position, defines a plane perpendicular to the holding member longitudinal axis can thus be pivoted such that, in the removal position, it is inclined relative to the described plane, in particular, is perpendicular thereto.

To enable conversion of the second tool element in the removal position into as compact a form as possible, it is advantageous for the surgical system to comprise a folding mechanism for transferring the second tool element from the operating position into the removal position. For example, a folding mechanism can be so configured that the second tool element itself, in turn, comprises two parts which are arranged or formed so as to be pivotable or otherwise movable relative to each other.

To enable the second tool element to be easily transferred from the operating position to the removal position and/or vice versa, it is expedient for the folding mechanism to comprise a force transmitting element for transmitting an actuating force onto the second tool element to transfer the second tool element from the operating position to the removal position and/or vice versa. With the force transmitting element, it is thus possible to actuate the folding mechanism which enables transfer of the second tool element from the operating position to the removal position and/or vice versa.

Preferably, the force transmitting element is arranged for movement relative to the holding member. For example, the second tool element can be moved into a desired position by the holding member, with actuation of the folding mechanism being possible by means of the force transmitting element which can be moved relative to the holding member.

In accordance with the use and design of the surgical system, it may be advantageous for the force transmitting element and the holding member to be configured for displacement and/or rotation and/or screwing relative to each other. Such an arrangement of the force transmitting element and the holding member relative to each other enables provision of practically any actuating mechanisms, for example, for actuating the folding mechanism.

In accordance with a preferred embodiment, it may be provided that the holding member and the force transmitting element are arranged for movement relative to the shaft. For example, the shaft can thus be held by a surgeon and the force transmitting element moved relative to the shaft, whereby, in particular, the folding mechanism can be actuated, in order to reduce the surface requirement for removing the second tool element. Owing to movability of the holding member and the shaft relative to each other, the tool elements can also be moved relative to each other in the operating position, whereby they can be transferred, for example, in order to connect tissue, into an approach position with as little spacing as possible, and can be moved apart again, for example, before transfer of the instrument from the operating position to the removal position.

In accordance with a further preferred embodiment, it may be advantageous for an actuating mechanism coupled with the folding mechanism and/or the force transmitting element and/or the holding member to be provided for actuating the folding mechanism and/or for moving the force transmitting element and/or the holding member relative to the shaft. The thus defined actuating mechanism allows, in accordance with the design of the instrument, the second tool element to be easily and safely moved from the operating position to the removal position and vice versa.

In order to facilitate and/or stabilize movement of the second tool element and the force transmitting element, it is expedient for the second tool element and the force transmitting element to be articulatedly coupled to each other by at least one articulation member. It is also conceivable to provide two, three or more articulation members.

To pivot the second tool element relative to the holding member, it is advantageous for the at least one articulation member to engage at one end the second tool element at an engagement or articulation point which is spaced from the pivot axis. A force required for pivoting the second tool element can thus be set in accordance with the choice of engagement or articulation point.

Advantageously, the second tool element is of two-part or multi-part configuration. In accordance with the configuration of the parts forming the second tool element, the second tool element can thus be converted into a particularly compact shape in the removal position.

In accordance with a further preferred embodiment, it may be provided that the second tool element comprises at least two tool element parts which are movable relative to each other during the transition from the operating position to the removal position. For example, they can be configured for displacement and/or rotation relative to each other, in order to reduce a surface of the second tool element in the removal position in comparison with the operating position.

The surgical system is particularly easy to construct when the at least two tool element parts are adapted for pivotal movement relative to each other. In particular, they can thus be easily collapsed.

To connect parts of tissue to one another by means of a current, which will also be referred to hereinbelow as welding or sealing, it is expedient for the second tool element to comprise an electrode element movable in the shaft direction and movable in the direction towards and away from the first tool element. In particular, the electrode element can carry a high-frequency electrode. The electrode element itself may, optionally, also be of two-part or multi-part configuration, in order to thereby reduce a space requirement for the second tool element in the removal position in comparison with the operating position.

It is advantageous for at least one of the high-frequency electrodes to be divided up into at least two electrode segments, and for the at least two electrode segments to be electrically insulated from each other. The division of at least one of the high-frequency electrodes into two or more electrode segments has, in particular, the advantage that the process parameters for connecting the parts of tissue to one another can be controlled significantly more easily. The smaller the surfaces between which the high-frequency current is used, the easier it is to control the process parameters. In particular, the temperature, pressure and tissue impendence have a considerable influence on the connecting results. For example, it is thus also possible to optimally and, in particular, also automatically adjust the process parameters to the nature of the tissue. Moreover, there is no need for any staples, which remain as foreign bodies in the body, as with a stapling device. In particular, the electrode segments dividing up the high-frequency electrode or the high-frequency electrodes make it possible for current to be applied segment-wise to the high-frequency electrode, so that the parts of tissue to be connected to one another can be welded or sealed segment-wise to one another. A segment-wise application of current made possible by the segmentation of the high-frequency electrodes allows less energy to be introduced into the parts of tissue during the connecting or sealing process than with comparable, unsegmented high-frequency electrodes. Furthermore, the segmentation has the advantage that areas of tissue between areas of the parts of tissue that have been connected by high-frequency current application remain unchanged and substantially undamaged, so that new cell growth starting from these is made possible, which, in addition to the connection made by the high-frequency current, enables a lasting connection of the parts of tissue by these growing together.

It is advantageous for the first tool element to comprise an edge surface of the shaft pointing in the distal or essentially in the distal direction. For example, a distal end of the shaft can thus be easily pressed or held against a part of tissue which is to be connected to another part of tissue. In addition, a defined tool element surface can also be easily and reliably prescribed.

It is expedient for contact members which, in a tissue-connecting position, are adapted to be brought into electrically conductive contact with the electrode segments of the second tool element and, in a tissue-gripping position, are spaced from the electrode segments of the second tool element to project on the shaft and/or on the first tool element and point in the direction towards the second tool element. With the contact members, it is possible to contact the electrode segments of the second tool element and to connect these to a current source, for example, a high-frequency generator, by an electrically conductive connection provided, for example, in the shaft. Furthermore, the proposed configuration has the advantage that contact between the electrode segments of the second tool element and the contact members can only be established in the tissue-connecting position, so that the electrode segments of the second tool element cannot accidentally have current applied to them in the tissue-gripping position. All in all, the handling of the surgical system is thereby made more reliable.

In order that the tool elements can be easily moved relative to each other, it is expedient for the instrument to comprise an actuating device for moving the tool elements relative to each other.

Expediently, at least one of the high-frequency electrodes is divided up into a plurality of electrode segments. In the context of this application, a plurality of electrode segments is to be understood as more than two electrode segments, which enable even further improved controllability of the process parameters.

Advantageously, electrode segments lying opposite each other and facing each other in the approach position form an electrode segment pair. Such an electrode segment pair can, for example, be controlled as a unit. In this way, in particular, local edge conditions in the region of the two electrode segments can be optimally taken into account, in particular, temperature, pressure and tissue impedance of tissue held between the electrode segment pair.

To enable the high-frequency current to be conducted, in a specially defined manner for connecting the tissue, from one electrode segment of the electrode segment pair to the associated electrode segment, it is expedient for the electrode segments forming the electrode segment pair to be geometrically similar.

The functionality of the system can be further improved, for example, by the electrode segments forming the electrode segment pair being of identical size or substantially identical size. In this way, in particular, current densities can be optimally prescribed.

The at least two electrode segments are of particularly simple design when they are strip-shaped or substantially strip-shaped.

In accordance with a preferred embodiment, it may be provided that each of the tool elements defines a tool element surface, and that the high-frequency electrode forms part of the tool element surface. This construction makes practically projection-free design of the tool elements possible.

It is expedient for the tool element surface, in the operating position, to define a projection surface or to extend parallel thereto. For example, the projection surface can be defined by the perpendicular projection. In particular, parts of tissue that are to be connected to one another can be uniformly held and pressed against each other when, in particular, the first tool element forms an end edge of a shaft of the instrument pointing in the distal direction.

Preferably, the tool element surface is flat. Manufacture and cleaning of the instrument are thereby significantly simplified.

In accordance with use of the surgical system, i.e., in particular, in accordance with the parts of tissue to be connected, it may be expedient for the tool element surface to be rectangular or ring-shaped. In particular, a ring-shaped tool element surface enables simple performance of end-to-end anastomoses.

It is advantageous for the at least two electrode segments to be arranged in at least two electrode rows adjacent to each other. At least two electrode rows make it possible to produce at least two connecting lines extending adjacent to each other. An improved connection and, in particular, an optimal sealing of the connection site between the parts of tissue can thereby be achieved. In particular, it is possible to maintain between the electrode rows, even after connection of the parts of tissue by high-frequency current application, completely or substantially intact cells, from which new cell growth can start. In the long term, this enables, in addition to the connecting of the parts of tissue by welding, a lasting connection of the parts of tissue by intact cells growing together.

Preferably, each electrode row comprises at least two electrode segments which are electrically insulated from each other. At least a sequential applying of current can thus be achieved.

In accordance with a further preferred embodiment, it may be provided that at least one electrode segment comprises a first electrode segment section which is part of a first electrode row, and a second electrode segment section which is part of a second electrode row. In this way, a double-row tissue connection can be produced, in particular, comprising or defining two connecting lines. Owing to the specially configured electrode segment sections, an even better overlapping is achieved between the two connecting lines, which, in particular, results in improved sealing of the tissue connection.

To enable connection of tissue in the shape of a ring, as is required, in particular, for end-to-end anastomoses, it is expedient for the at least two electrode rows to be of self-contained, ring-shaped configuration.

In order that current can be individually applied to each electrode segment, as required, it is advantageous for each electrode segment to be electrically conductively connected to a connecting contact. The connecting contact can, in turn, be connected to other connecting contacts or be directly connected or connectable to a current source.

In accordance with a further preferred embodiment, it may be provided that the at least one high-frequency electrode divided up into at least two electrode segments defines an electrode length, and that each of the at least two electrode segments defines a segment length which is smaller than the electrode length. With this construction, it can, in particular, be ensured that only a section of the parts of tissue to be joined together that is smaller than a total length of the high-frequency electrode can be connected with each electrode segment.

To improve the tightness of a connection site produced by the surgical system between two parts of tissue, it is expedient for the sum of all segment lengths to be greater than the electrode length. This ensures at least partially an overlapping of tissue connections produced with the electrode segments.

To enable simple and safe connection of the instrument to a high-frequency generator or to any other suitable high-frequency current source, it is expedient for the instrument to comprise at least two high-frequency connecting contacts which are electrically conductively connected or connectable to the at least two electrode segments.

To enable tissue to be gripped between the two tool elements and possibly held during the connecting process, it is advantageous for the tool elements to be configured for pivotal movement and/or displacement relative to each other. All in all, a movable arrangement of the tool elements relative to each other is desirable.

It is expedient for contact members which, in a tissue-connecting position, are adapted to be brought into electrically conductive contact with the electrode segments of the second tool element and, in a tissue-gripping position, are spaced from the electrode segments of the second tool element to project on the shaft and/or on the first tool element and point in the direction towards the second tool element. With the contact members, it is possible to contact the electrode segments of the second tool element and to connect these to a current source, for example, a high-frequency generator, by an electrically conductive connection provided, for example, in the shaft. Furthermore, the proposed configuration has the advantage that contact between the electrode segments of the second tool element and the contact members can only be established in the tissue-connecting position, so that the electrode segments of the second tool element cannot accidentally have current applied to them in the tissue-gripping position. All in all, the handling of the surgical system is thereby made more reliable.

In order that the tool elements can be easily moved relative to each other, it is expedient for the instrument to comprise an actuating device for moving the tool elements relative to each other.

For further improvement of the handling of the surgical instrument, the actuating device is preferably arranged or formed at a proximal end of the instrument. For example, when the instrument comprises a shaft, this can be introduced through an opening in the body into the interior of the body, and the tool elements are then actuatable relative to each other by the actuating device which, preferably, still protrudes from the patient's body. All in all, an endoscopic or minimally invasive surgical instrument can thus be formed in a simple way.

The handling of the instrument can be improved for a surgeon, in particular, by the actuating device comprising two actuating members pivotable relative to each other, which are in operative connection with at least one of the tool elements for transmission of an actuating force for moving the at least one tool element relative to the other tool element. In principle, the actuating members can also be configured for movement relative to each other only, i.e., alternatively to a pivotable arrangement, for example, they can also be arranged displaceably or pivotably and displaceably relative to each other.

In accordance with a further preferred embodiment, it is advantageously provided that the instrument comprises a high-frequency cutting element for severing tissue. Provision of a high-frequency cutting element which, for example, can be part of a cutting device of the instrument, enables, in particular, parts of tissue connected to one another to be prepared in a desired manner. For example, this may be the case when end-to-end anastomoses are to be produced with the system, where free ends of tubular tissue are connected in the shape of a ring by the instrument and protruding tissue is then cut off by the cutting element or the cutting device.

Preferably, the high-frequency cutting element comprises a cutting edge which defines a cutting plane inclined relative to a longitudinal axis of the instrument, in particular, in the region of the high-frequency cutting element. Owing to the inclined cutting plane, a high-frequency current, for example, can be conducted across the cutting element in order to sever tissue. Only in a small region is the thus formed cutting edge then spaced at a minimum distance from a counter electrode defining a plane transverse to the longitudinal axis of the instrument. A cutting spark can thus be generated in a defined manner in the region of the shortest distance between the high-frequency cutting element and a corresponding counter electrode, and the cutting spark can then travel in a defined manner along the inclined cutting edge.

To enable a ring-shaped cut to be easily and reliably made, the cutting edge is expediently closed in the shape of a ring.

In order that a high-frequency current can be applied to the high-frequency cutting element in a defined manner, it is advantageous for the instrument to comprise a high-frequency cutting connection which is electrically conductively connected to the high-frequency cutting element. In particular, with such a configuration a high-frequency current can be applied in a defined manner to the high-frequency cutting element to sever tissue, preferably independently of and at different times from applying a high-frequency current to the electrode segments to connect the parts of tissue to one another.

It is advantageous for the cutting element to be arranged for movement relative to at least one of the tool elements. This makes it possible, for example, to move the cutting element relative to the tool elements in such a way that it cannot come into contact with the parts of tissue to be connected to one another when these are being connected by means of the electrode segments formed on the tool elements. Rather, only after connection of the parts of tissue is it thus possible, for example, to move the cutting element into a position in which these can be cut and/or completely or partly severed in a desired manner.

To enable application of a high-frequency current to the high-frequency instrument in a desired manner, the surgical system preferably comprises at least one high-frequency current generator which is selectively electrically conductively connectable to the high-frequency electrodes and/or the cutting element. In particular, it is thus possible to set the respective optimum current for the connecting or severing of tissue.

In accordance with a further preferred embodiment, it may provided that the system comprises at least one control device with a switching device for sequentially applying high-frequency current to the electrode segments of at least one high-frequency electrode. Optionally, high-frequency current can also be applied to a further high-frequency electrode with the control device. With the switching device configured in the described manner, in particular, a high-frequency current can be applied to the electrode segments of a high-frequency electrode one after the other, i.e., in a sequential order, for section-wise connection of the parts of tissue to be joined together.

It is expedient for the surgical system to comprise a control device with a switching device for simultaneously applying high-frequency current to at least two electrode segments of at least one high-frequency electrode. In this way, the connecting or sealing process can be accelerated or performed more quickly as two parts of tissue to be joined together can be simultaneously connected to each other along two sections. In particular, it is also conceivable to simultaneously apply a high-frequency current to two electrode segments, and to then sequentially apply a high-frequency current to further electrode segments.

To avoid short circuiting when high-frequency current is simultaneously applied to two electrode segments, it is expedient for at least one further electrode segment to be arranged between the at least two electrode segments.

It is expedient for the switching device to be configured for switching at least one high-frequency output of the at least one current generator. It is also possible to provide two, three or even more high-frequency outputs, which can be controlled by the switching device, in order, for example, to specifically apply to individual electrode segments of the high-frequency electrodes a high-frequency current of a desired strength.

It is advantageous for the surgical system to comprise a high-frequency generator which is selectively electrically conductively connectable to the high-frequency electrodes or the cutting element and comprises the control device. In this way, several functions of the system can be accommodated in one apparatus, which improves both its manufacture and its handling.

Expediently, the control device is so configured that a strength of the current applied and/or a duration of the current application is settable for the individual electrode segments. In this way, in particular, process parameters such as temperature, pressure and tissue impedance can be kept directly or indirectly within the desired range by the control device.

To avoid excessive heating of the parts of tissue to be joined together, which would result in destruction of cells, it is advantageous for the control device to comprise a temperature measuring device for measuring an electrode segment temperature and/or a tissue temperature.

It is also expedient for the control device to comprise an impedance measuring device for measuring a tissue impedance of tissue held between the tool elements. The determining of the tissue impedance offers the possibility of controlling the current or high-frequency generator, in particular, the power provided by it as a function of its value. In this way, the energy to be introduced into the parts of tissue in order to connect them can be easily and reliably controlled. In particular, the high-frequency electrodes can be used to measure the tissue impedance. A measurement can also take place between individual electrode segments that lie opposite each other. Preferably, the tissue impedance is measured while current is not being applied to the high-frequency electrodes. In particular, it is expedient to measure the tissue impedance during the breaks when changing the polarity of the high-frequency current. The change in the tissue can then be monitored very well and practically in real time and further energy input can be stopped or specifically allowed to continue.

The following description of preferred embodiments of the invention serves in conjunction with the drawings for further explanation.

A surgical system for connecting body tissue is diagrammatically represented and generally designated by reference numeral 10 in FIG. 1. It comprises a surgical instrument 12 with two tool elements 14 and 16 which are movable relative to each other. The system 10 further comprises a current generator in the form of a high-frequency current generator 18, which can be connected to the instrument 12 in a manner described in more detail hereinbelow.

The tool elements 14 and 16 form part of a connecting device generally designated by reference numeral 20 for connecting body tissue. The first tool element 14 has an edge surface 42, pointing in the distal direction, of an elongate, sleeve-shaped shaft 24 of the instrument 12. The first tool element is thus arranged or formed at a distal end 26 of the instrument 12.

The first tool element 14 comprises a high-frequency electrode 28. It is divided up into at least two, in the embodiment represented diagrammatically in FIGS. 2 to 5 into four, electrode segments 30 which are electrically insulated from one another. The electrode segments 30 are of strip-shaped or substantially strip-shaped configuration. The first tool element 14 defines a tool element surface 32 in such a way that the high-frequency electrode 28 forms part thereof. The tool element surface 32 is of overall flat and ring-shaped configuration.

The four electrode segments 30 define two electrode rows 34 and 36. Each electrode row comprises part of the four electrode segments 30. As is apparent from FIG. 5, for example, each electrode segment 30 has a first electrode segment section 38 forming part of the first electrode row 34, and a second electrode segment section 40 forming part of the second electrode row 36. The two electrode rows 34 and 36 are of overall curved configuration, and the electrode segment sections 38 and 40 each define electrically conductive circular ring sections. The at least two electrode rows, which are each defined by four electrode segment sections 38 and 40, respectively, are overall of self-contained, ring-shaped configuration. To enable the electrode segments 30 to be contacted in a desired manner, each electrode segment 30 is electrically conductively connected to a connecting contact 42 which is arranged in a connection region between the electrode segment sections 38, 40. Even after connection of the parts of tissue by applying high-frequency current, there still remain between the electrode rows completely or substantially undamaged cells from which new cell growth can start. In the long term, this enables, in addition to the connection of the parts of tissue by welding, a lasting connection of the parts of tissue by intact cells growing together.

The high-frequency electrode 28 defines an electrode center line 44 extending between the electrode segment sections 38 and 40. Adjacent electrode segments 30 are therefore arranged offset from one another in a direction defined by the electrode center line 44. The high-frequency electrode 28 divided up into four electrode segments 30 defines overall an electrode length 46, each of the four electrode segments 30 defining a segment length 48 which is smaller than the electrode length 46. As shown, for example, in FIG. 5, the electrode segments 30 extend over an angular range of approximately 140° and therefore have a length which corresponds approximately to 40% of the electrode length 46. Therefore, the sum of all segment lengths 48 exceeds the electrode length 46 by approximately the factor 1.6.

In the region of a proximal end of the shaft 24, high-frequency connecting contacts 50 are arranged, which are electrically conductively connected, for example, by lines extending in the shaft, to the electrode segments 30. Preferably, the number of high-frequency connecting contacts 50 corresponds to the number of electrode segments 30, i.e., four high-frequency connecting contacts 50 for the four electrode segments 30 of the first tool element 14.

The second tool element 16 is of substantially disc-shaped configuration and comprises an electrode element 52, which is movable in the direction towards the first tool element 14 and away from it, more specifically, parallel to a longitudinal axis 54 of the shaft 24 in the region of the tool elements 14, 16, which defines a shaft direction 56. The tool elements 14, 16 are arranged for displacement relative to each other, i.e., a distance 58 between the tool element surface 32 of the first tool element 14 and a tool element surface 60 of the second tool element 16 is alterable.

The electrode element 52 comprises a high-frequency electrode 29, which corresponds in its construction to the high-frequency electrode 28. This means that it also comprises four electrode segments 31, which do not project over the tool element surface 60. Two electrode rows 35 and 37 are also defined, first electrode segment sections 39 defining the electrode row 35, and second electrode segment sections 41 defining the electrode row 37. Connecting contacts 43 are also provided, which each conductively connect an electrode segment section 39 to an electrode segment section 41 to form an electrode segment 31. The high-frequency electrodes 28 and 29 are formed mirror-symmetrically in relation to a mirror plane extending perpendicularly to the longitudinal axis 54 between the tool element surfaces 32 and 60. In this way, electrode segment pairs 62 are defined, in each case, by an electrode segment 30 and the corresponding opposite electrode segment 31. All in all, the embodiment shown in FIGS. 1 to 5 therefore comprises four electrode segment pairs 62. The electrode segments 30, 31 are not only similar geometrically, but are of the same size or substantially the same size.

In an approach position of the tool elements 14, 16, the high-frequency electrodes 28, 29 define a minimum distance 58 from each other. The approach position is shown diagrammatically in FIG. 4. In the approach position, the high-frequency electrodes 28 and 29 lie opposite each other and face each other.

The electrode segments 31 are electrically conductively connectable to further four high-frequency connecting contacts 50, only two of which are shown in FIG. 1 for reasons of clarity. The high-frequency connecting contacts 50 can be connected by corresponding connection lines 64 to corresponding contacts 66 of the high-frequency current generator 18. As explained above, the high-frequency connecting contacts 50 are directly electrically conductively connected to the electrode segments 30. To enable the high-frequency connecting contacts 50 to be connected to the electrode segments 31, there are arranged on the shaft 24 or on the first tool element 14 so as to protrude in the direction facing the second tool element 16 contact members 68, which have a short cylindrical section 70 and a conical section 72 defining a free end. In a tissue-connecting position, as shown, for example, diagrammatically in FIG. 4, i.e., in a position in which the tool elements 14 and 16 are in an approach position, the free ends of the sections 72 of the contact members 68 extend into corresponding bush-shaped receptacles 74 of the electrode element 52 and are in electrically conductive contact with these. The contact members 68, in turn, are connected along the shaft 24 by electric lines, not shown, to the high-frequency connecting contacts 50. The receptacles 74 are, in turn, electrically conductively connected to the connecting contacts 43. In this way, an electrically conductive contact between the high-frequency connecting contacts 50 and the electrode segments 31 can also be established in the approach position or tissue-connecting position.

Of course, the contact members 68 which extend through the electrode segments 30 in the region of their connecting contacts 42 are insulated from these so that short circuiting cannot occur. For this purpose, the sections 70 of the contact members 68 are preferably provided with an electrically insulating coating or sheath.

To enable movement of the tool elements 14, 16 of the instrument 12 relative to each other, an actuating device 76 is arranged at a proximal end or end region of the instrument 12. The actuating device 76 comprises two actuating members 78 pivotable relative to each other, which are movably coupled to a force transmitting member 80 movably mounted inside the shaft, so that as a result of a pivotal movement of the actuating members 78, the force transmitting member 80 is movable in the distal or proximal direction.

The force transmitting member 80 defines at its distal end a blind hole-shaped receptacle 82 into which a holding member 84 is introducible with a first free end and fixable in the receptacle 82. The second free end of the substantially rod-shaped holding member 84 is immovably connected to the second tool element 16. In this way, as a result of displacement of the force transmitting member 80 in the distal direction, the second tool element 16 can be moved away from the first tool element 14. Preferably, the instrument 12 is so constructed that the second tool element 16 can be moved from a tissue-gripping position, as represented diagrammatically in FIGS. 2 and 3, and in which the tool elements 14, 16 are at a maximum distance 58 from each other, into the approach position or tissue-connecting position by pivoting the actuating members 78 towards each other, which results in movement of the force transmitting member 80 in the proximal direction.

Furthermore, the instrument 12 comprises a cutting device 86 for severing tissue. The cutting device comprises a cutting element 88 with a self-contained ring-shaped cutting edge 90. The cutting edge 90 defines a cutting plane 92 inclined relative to the longitudinal axis 54 of the instrument 12. The cutting plane 92 is inclined through approximately 10° in relation to a reference plane extending perpendicularly to the longitudinal axis 54 and running parallel to the tool element surfaces 32 and 33. At the proximal end of the shaft 24 a further high-frequency cutting connection 94 is provided, which in a variant of the instrument 12 is electrically conductively connected to the cutting element 88. It is, for example, thus possible to provide a monopolar cutting device 86. In the conventional manner, a neutral electrode has then to be applied to the patient's body for monopolar cutting. A bipolar cutting device 86 is provided, for example, by arranging on the second tool element 16, opposite the cutting edge 90, a ring electrode 96 which is connected to a further high-frequency cutting connection 94 by an electrically conductive connection, not shown in greater detail, which, for example, in a manner not shown in greater detail, runs through the force transmitting member 80. Optionally, the ring electrode 96 itself can also be segmented, for example, in analogy with the high-frequency electrodes 28 and 29. It is also possible, instead of the ring electrode 96, to use the high-frequency electrode 29 as counter electrode.

The cutting element 88 is preferably mounted for displacement relative to the two tool elements 14, 16. The cutting edge 90 formed concentrically around the longitudinal axis 54 can thus be displaced relative to the high-frequency electrodes 28 and 29. A cutting-actuator 98 with an actuating member 100 protruding from the proximal end of the instrument is provided for actuating the cutting device 86. The actuating member 100 is mechanically coupled to the cutting element 88 by a mechanism, not shown, for example, a further force transmitting member extending inside the shaft 24, so that movement of the actuating member 100 also causes the cutting element 88 to be moved. Preferably, the actuating member 100 is arranged for displacement and rotation relative to the shaft 24, so that the cutting element 88 is not only displaceable parallel to the longitudinal axis 54 but also rotatable relative thereto.

A control device 102 with a switching device 104 is provided for applying a high-frequency current to the electrode segments 30, 31 in any desired manner. The control device 102 is preferably arranged in a housing of the high-frequency current generator 18 and forms part thereof. In particular, the switching device 104 is configured for sequentially applying a high-frequency current to the electrode segments 30, 31. The switching device 104 serves, in particular, to control the contacts 66 and further contacts 106, which are connectable by further connection lines 108 to the high-frequency cutting connections 94 of the instrument 12. In this way, the cutting device 86 can be operated in a monopolar or bipolar manner with the high-frequency current generator 18. For monopolar operation, high-frequency current is merely applied to the cutting element 88 and a neutral electrode as counter electrode is placed on the patient's body. For bipolar cutting, in particular, a ring-shaped counter electrode can be provided on the second tool element 16, for example, in the form of the ring electrode 96, so that a high-frequency current can then flow between the counter electrode and the cutting element 88. Alternatively, the high-frequency electrode 29 can also be used as counter electrode. If application of current to the cutting device 86 is dispensed with completely, it can then also be used purely mechanically for severing tissue, more specifically, with the preferably sharpened cutting edge 90.

Furthermore, the switching device 104 can also be so configured that a high-frequency current can be simultaneously applied to at least two electrode segments 30, 31 of a high-frequency electrode 28, 29. In this case, it is expedient to respectively arrange between two electrode segments 30, 31 to which high-frequency current is simultaneously applied a further electrode segment 30, 31, to which current is then not applied. For example, in this way, the opposite electrode segments 30 of the high-frequency electrode 28 shown in FIG. 5 could have current applied to them simultaneously, and the two other electrode segments 30 then do not have current applied to them.

To enable individual setting of the strength and/or duration of the current application to the individual electrode segments 30, 31, the control device 102 is configured so as to comprise a setting device 110. For example, a strength and/or a frequency of the high-frequency current as well as a duration of the current application can be set by the setting device 110. Furthermore, the setting device 110 may also be optionally configured so as to enable individual setting of current application sequences.

Furthermore, the control device 102 preferably comprises a temperature measuring device 112 for measuring an electrode segment temperature and/or a tissue temperature. The temperature measuring device 112 serves, in particular, to supply the control device 102 with the control variable required for automatic control of current application to the high-frequency electrodes 28, 29, namely a temperature of the tissue, for example, indirectly by means of a temperature measurement of the electrode segments 30, 31. For example, electrode segments 30, 31 to which current is not applied can serve as measuring contacts for temperature detection by means of tissue impedance measurement. In this way, it can be ensured that the temperature required for connecting the tissue is reached in the desired manner and with high precision by appropriate application of current to the high-frequency electrodes 28, 29, but undesired overheating of the parts of tissue to be connected to one another is avoided.

Furthermore, the control device 102 optionally comprises an impedance measuring device 113 for measuring a tissue impedance of tissue held between the tool elements 14 and 16. The determining of the tissue impedance offers the possibility of controlling the high-frequency generator 18, in particular, the parameters voltage, current or power provided by it, as a function of its value. In this way, the energy to be introduced into the parts of tissue to connect these can be easily and reliably controlled. In particular, the high-frequency electrodes 28 and 29 can be used for measuring the tissue impedance. A measurement can also take place between individual electrode segments 30 and 31 lying opposite one another. The measurement of the tissue impedance can take place selectively while current is being applied to the high-frequency electrodes 28, 29 or when current is not being applied to the high-frequency electrodes 28, 29. The change in the tissue can thus be monitored very well and practically in real time, and further energy input metered, stopped or specifically allowed to continue.

Figure 3:
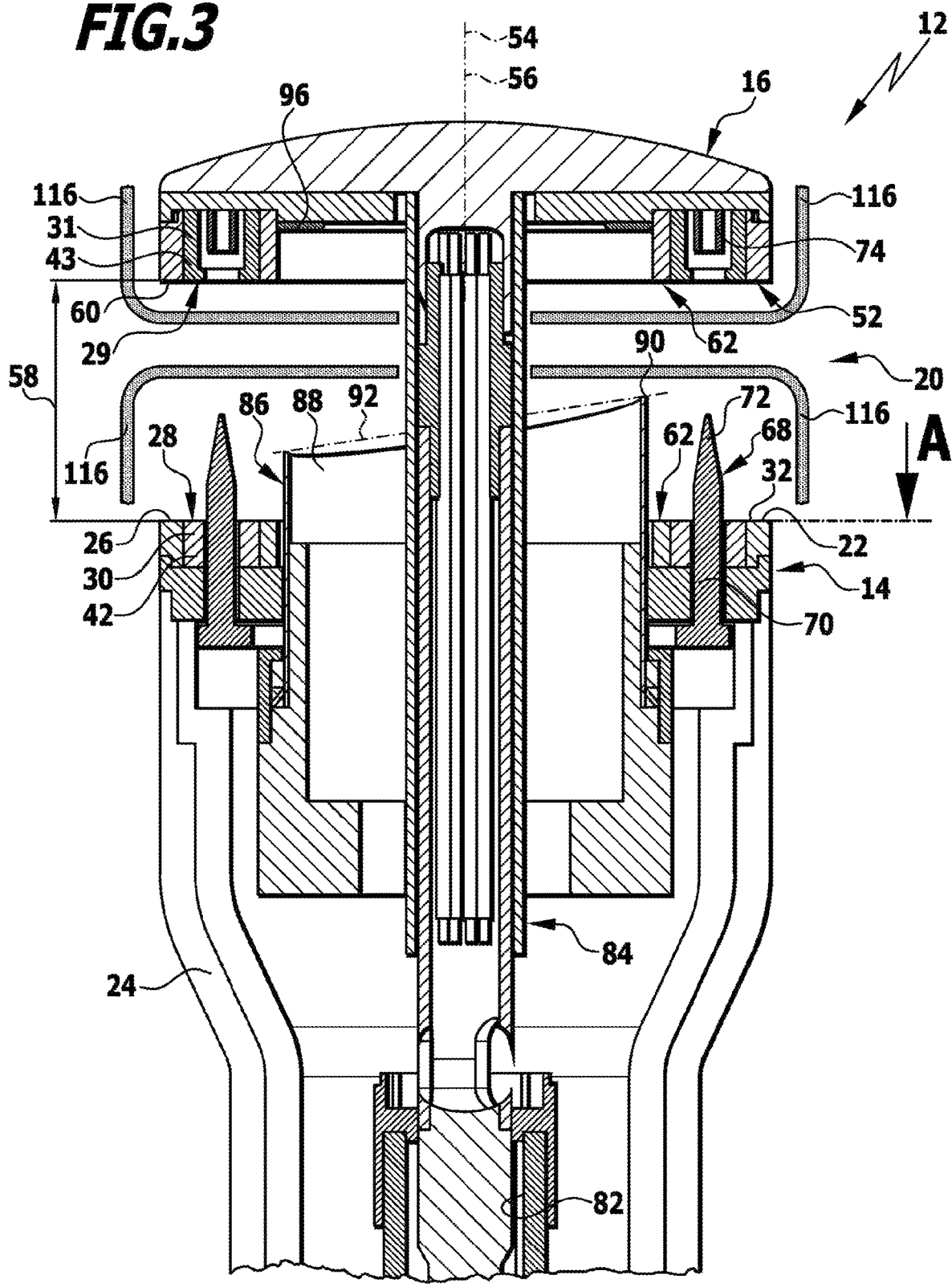
FIG. 3 shows a longitudinal sectional view of the instrument from FIG. 1 in area A prior to connection of two tubular parts of tissue.
Figure 4:
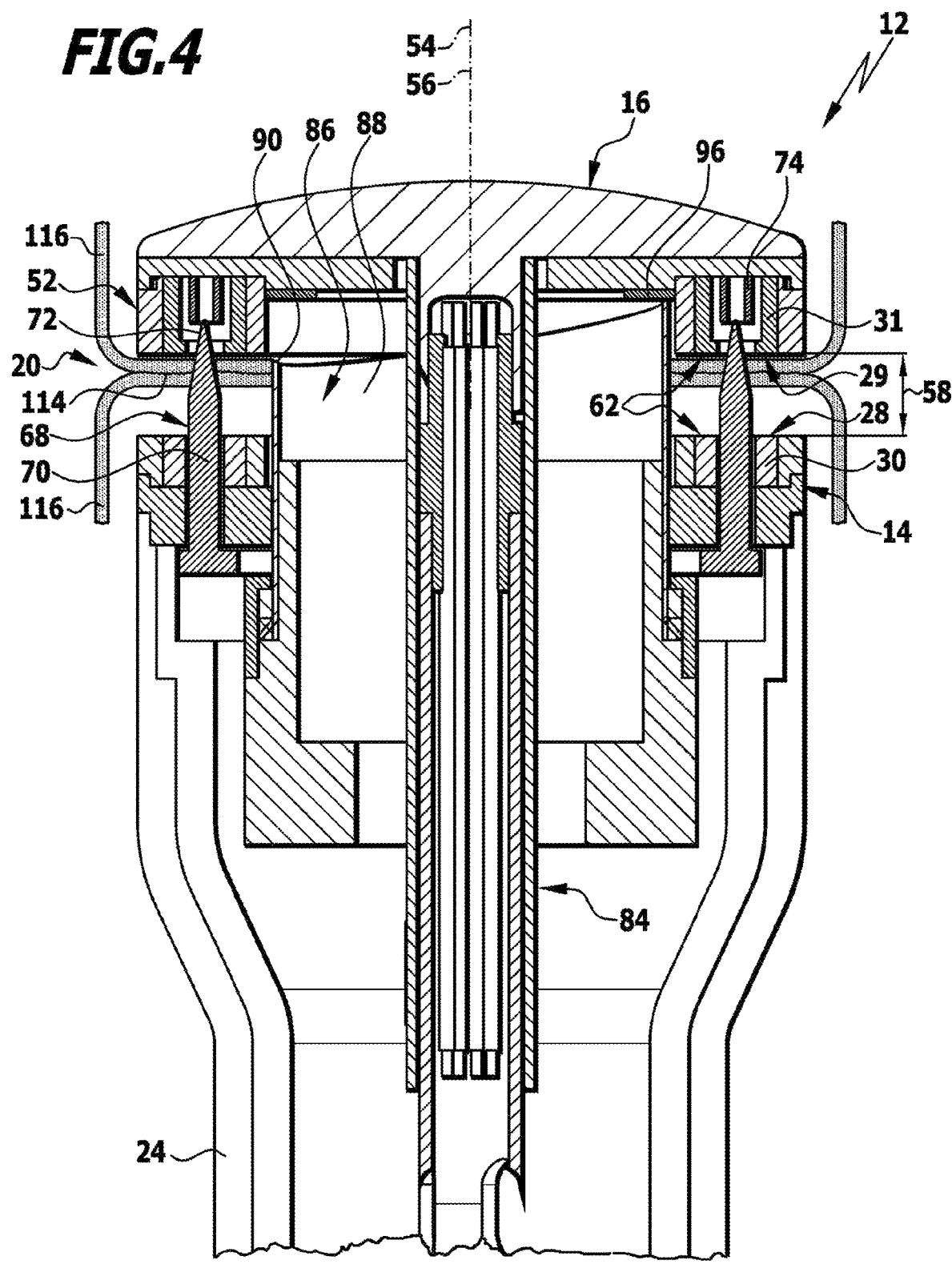
FIG. 4 shows a view in analogy with FIG. 3 during the welding of the parts of tissue to produce an end-to-end anastomosis.
Figure 5:
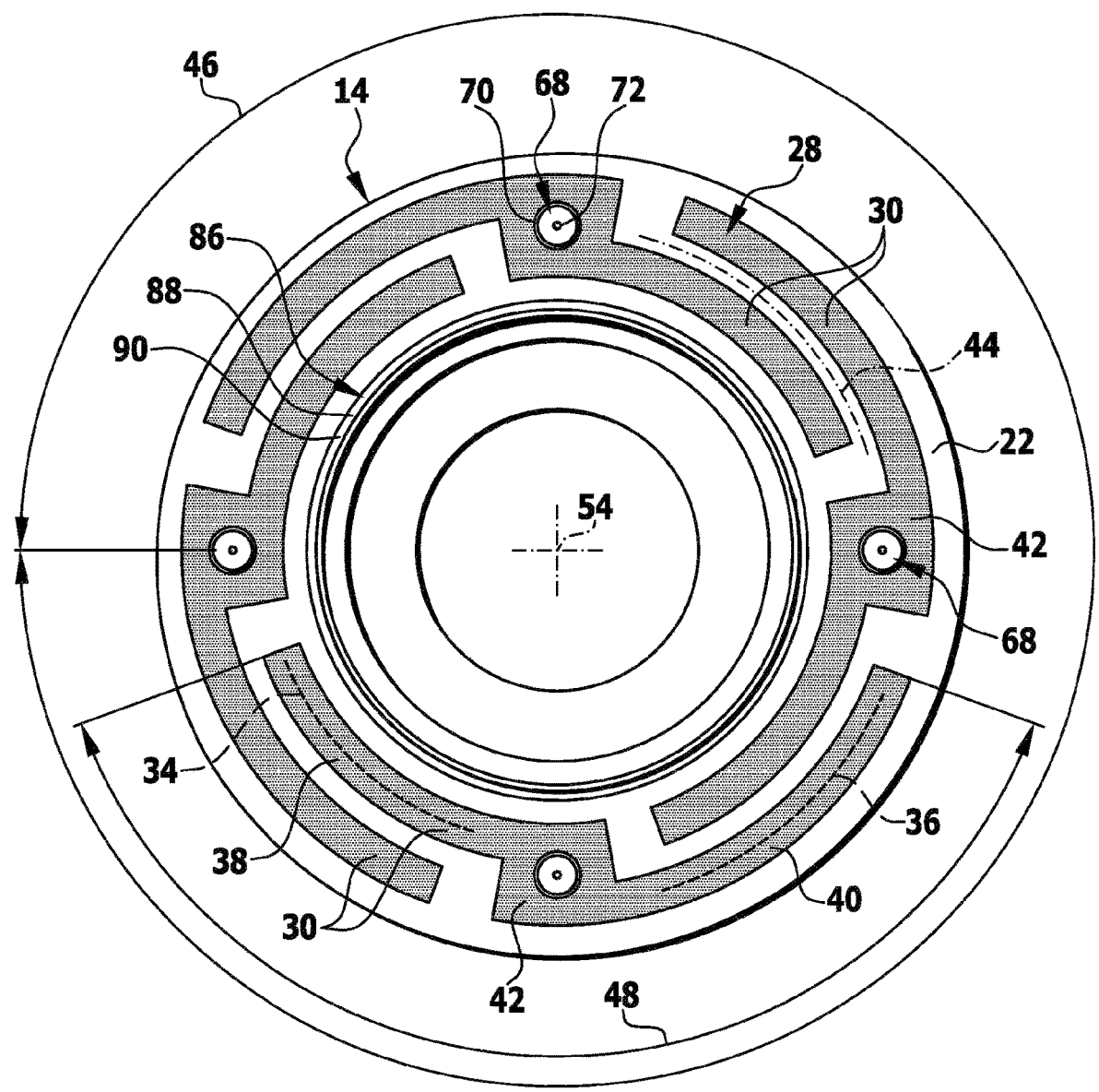
FIG. 5 shows a plan view of a tool element surface with a high-frequency electrode divided up into four electrode segments.

With the surgical system 10 described above, in particular, tubular parts of tissue 116 can be directly connected to one another by these being welded or sealed to one another by the application of high-frequency current. The procedure is, for example, as follows:

To produce an end-to-end anastomosis of two tubular parts of tissue 116, as is required, for example, after intestinal surgery, during which part of the intestine is removed, free ends of the parts of tissue 116 are brought close together, so that with their free ends facing in the direction towards the longitudinal axis, they lie with surface-to-surface contact in ring-shaped configuration against one another, as shown, by way of example, in FIGS. 3 and 4. The free ends are then located between the two tool elements 14, 16, so that the parts of tissue 116 can be held clamped against one another between the tool elements 14, 16 in the tissue-gripping position.

The tool elements 14, 16 are then moved towards each other into the tissue-connecting position, so that the electrode segments 31 are also electrically conductively connected to the high-frequency connecting contacts 50 in the manner described above. To weld the parts of tissue 116, a high-frequency current is now preferably applied to individual electrode segment pairs 62. It then flows over the sections of the parts of tissue held between the tool elements 14, 16 and heats these. At a temperature of from approximately 50° C. to approximately 80° C., preferably from approximately 65° C. to approximately 70° C., such a change takes place in the cells that the parts of tissue 116 adhere to one another. The connecting method is preferably carried out such that always only one electrode segment pair 62 has current applied to it at a time, in particular, in a sequential order. In this way, a ring-shaped connecting line 114 is created, which is substantially predetermined by the high-frequency electrodes 28, 29 or their electrode center lines 44, 45.

Owing to the fact that a high-frequency current is not applied to the entire high-frequency electrodes 28, 29, the temperature for connecting the parts of tissue 116 can be controlled much better and destruction of the cells prevented. Preferably, current is applied to the electrode segments 30, 31 one after the other, i.e., sequentially, so that the parts of tissue 116 are welded to one another step-by-step along the connecting line 114. Furthermore, owing to the arrangement of the electrode segment sections 38, 39, 40 and 41 in two rows, a double connection is made between the parts of tissue 116, which ensures optimum sealing and a lasting, stable connection of the parts of tissue 116 to one another.

As an alternative to sequential application of current, as indicated above, opposite electrode segments 30, 31 can also have current applied to them simultaneously. The time for connecting the parts of tissue 116 can thereby be halved in the embodiment represented diagrammatically in FIGS. 1 to 5.

After connection of the parts of tissue 116, projecting tissue is removed with the cutting device 86. The cutting device 86 is preferably used in a bipolar manner, i.e., the cutting element 88 and the ring electrode 96 are connected to the high-frequency current generator 18 and high-frequency current is passed over the two parts of tissue 116 to sever the tissue. Owing to the inclined cutting edge 90, a defined cutting spark is generated, more specifically, in the region in which the distance between the cutting edge 88 and the ring electrode 96 is minimal. Starting from this region, the cutting spark then automatically travels along the cutting edge 90 in a circle in both directions until the tissue is completely severed. Use of the cutting device 86 in bipolar operating mode has, in particular, the advantage that when being severed, the parts of tissue 116 are simultaneously also coagulated in order to stop any undesired bleeding directly during the severing.

After connecting and cutting the parts of tissue 116, the instrument 12 can then be withdrawn by retracting the shaft 24 from the patient's body, for example, from his intestine.

In accordance with the design of the instrument 12, the shaft 24 is preferably of such length that during use of the instrument 12 both the actuating device 76 and the cutting-actuator 98 still protrude from the patient's body so that they can be actuated by a surgeon.

Figure 6:
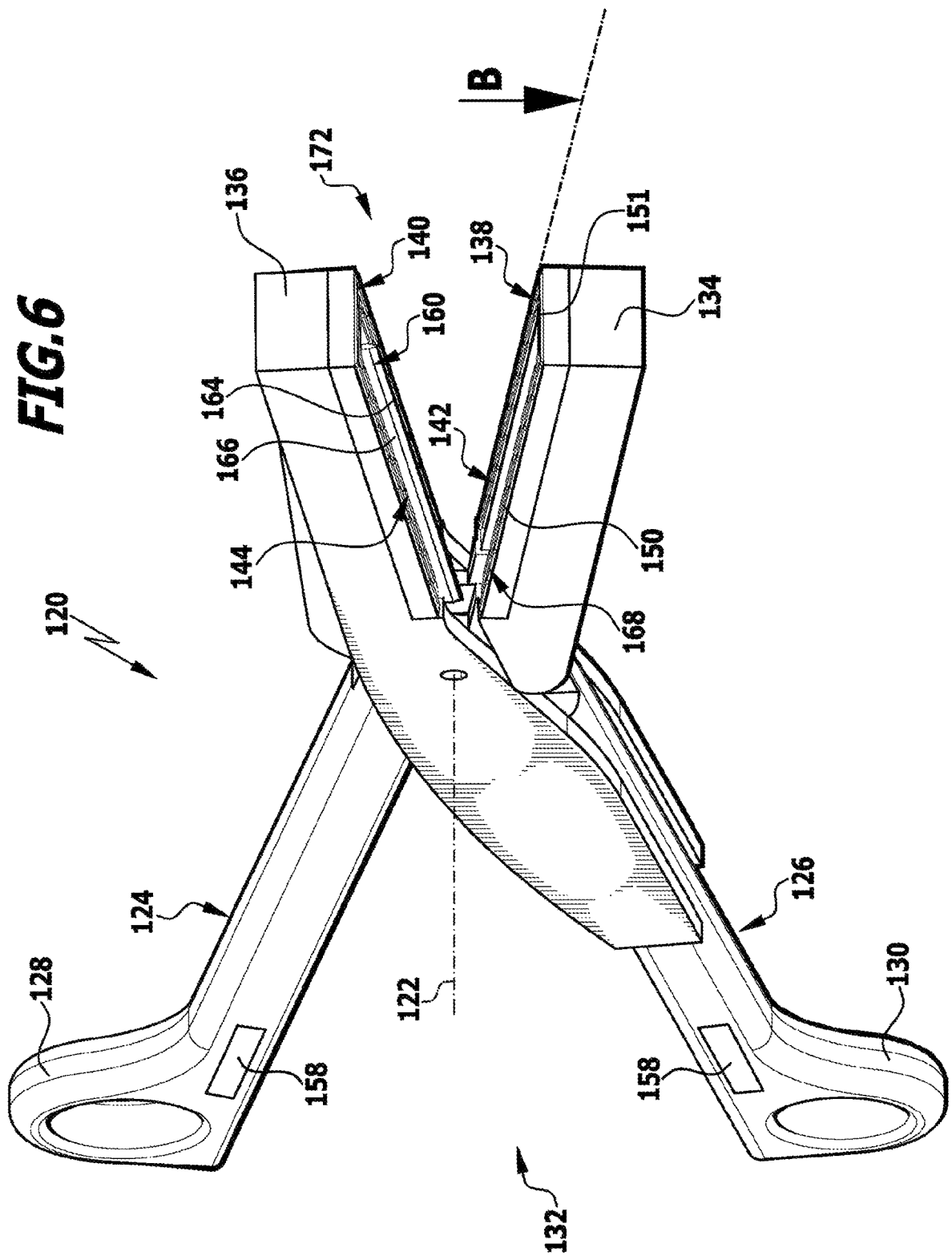
FIG. 6 shows a perspective, diagrammatic view of a second embodiment of a surgical instrument for connecting parts of body tissue.
Figure 7:
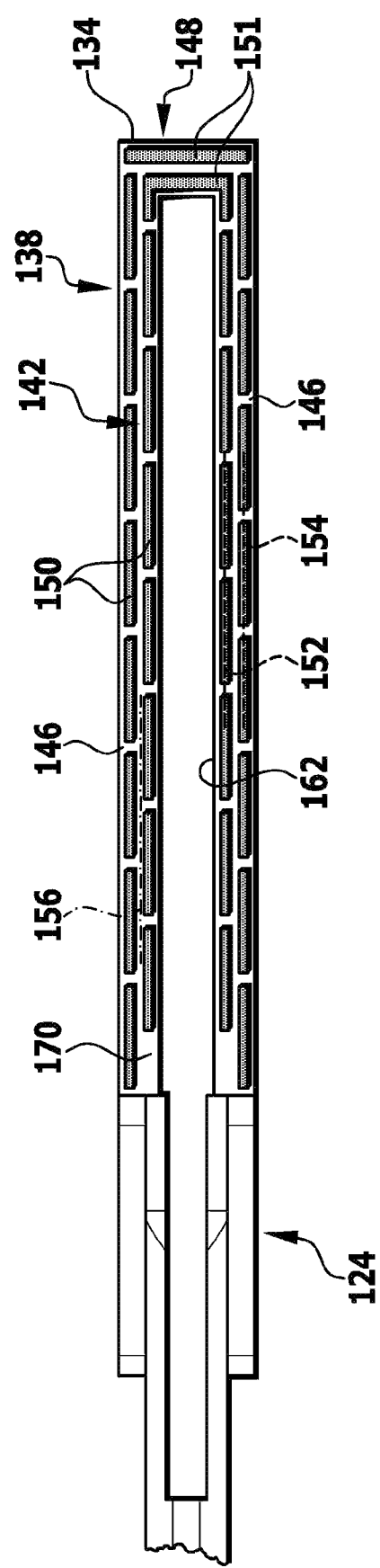
FIG. 7 shows a plan view of a diagrammatically represented tool element surface of the instrument from FIG. 6 in the direction of arrow B.
Figure 8:
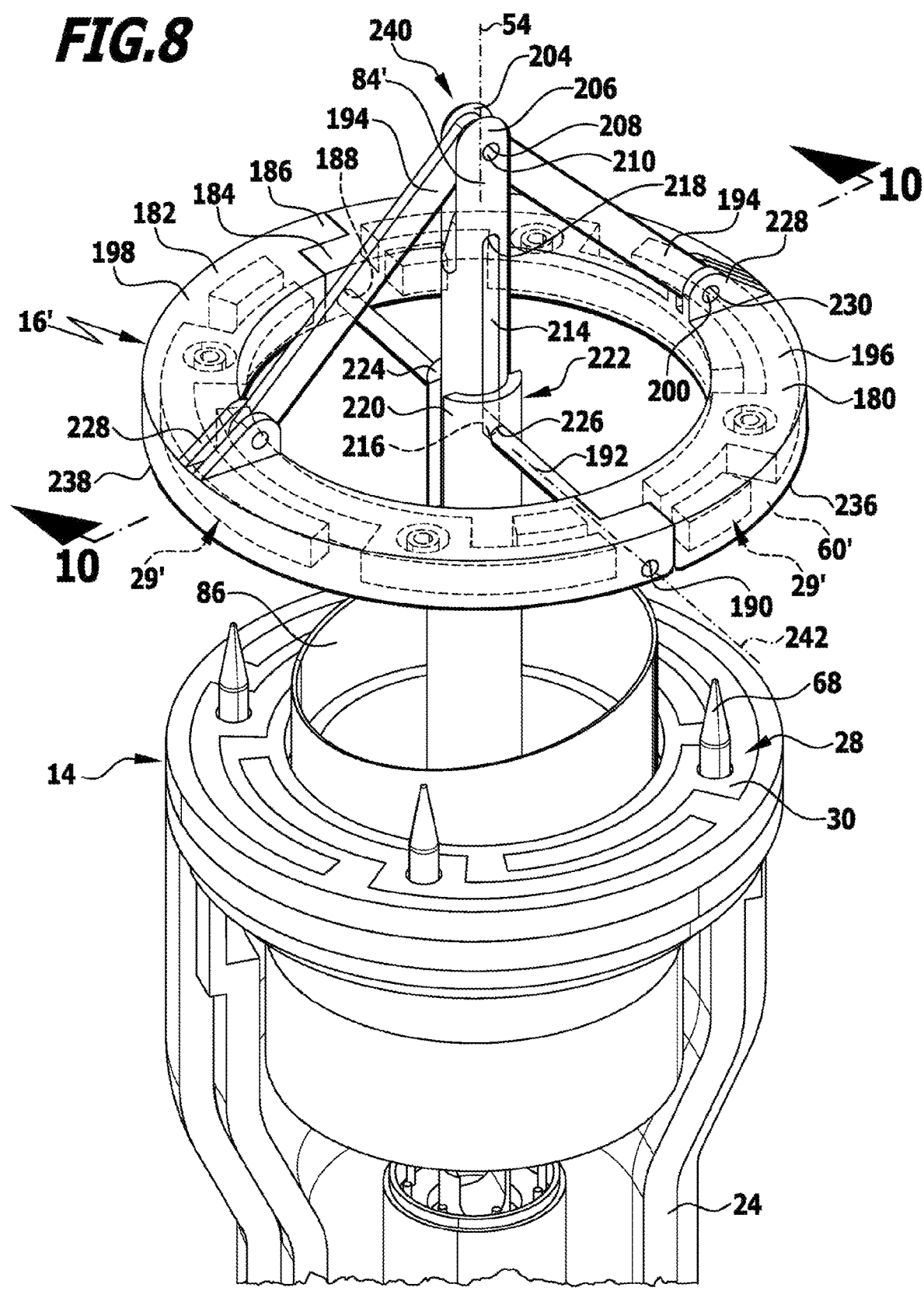
FIG. 8 shows a diagrammatic view similar to FIG. 2 of an alternative configuration of the instrument in a tissue-gripping position.

Alternatively or additionally, the surgical system 10 can comprise, instead of the instrument 12, a surgical instrument, for example, in the form of an instrument 120 represented diagrammatically in FIGS. 6 and 7. The instrument 120 comprises two arms 124 and 126 mounted on each other for pivotal movement relative to each other about a pivot axis 122. At a proximal end of the arms 124, 126, finger rings 128, 130 are formed, which together define an actuating device 132 for actuating the instrument 120.

Starting from free, distal ends 134 and 136 of the arms 124 and 126, tool elements 138 and 140 are formed on inner sides thereof so as to face each other. The tool elements 138 and 140 are of identical construction and, in an approach position of the ends 134 and 136, are located opposite each other and, in this position, are at a minimum distance from each other. Each tool element 138, 140 comprises a high-frequency electrode 142, 144. These are of identical, substantially U-shaped construction. Each high-frequency electrode 142, 144 comprises two electrode sections 146 extending parallel to each other in a direction perpendicular to the pivot axis 122 and an electrode section 148 extending perpendicular to these and adjoining the ends 134, 136.

The construction of the high-frequency electrodes 142, 144 will be described in greater detail hereinbelow, by way of example, in conjunction with FIG. 7 with reference to the high-frequency electrode 142.

The high-frequency electrode 142 comprises a total of 30 electrode segments 150. In each case, 15 electrode segments are arranged offset from one another in two electrode rows 152, 154 parallel to one another along each electrode section 146 and are electrically insulated from one another. The electrode segments 150 are of straight-lined and strip-shaped configuration. They define between them an electrode center line 156 which in accordance with the shape of the high-frequency electrode 142 is also of U-shaped configuration. Two further electrode segments 151 are arranged in the region of the electrode section 148 and complete the electrode rows 152 and 154, respectively, of the electrode sections 146. The electrode segments 150 and 151 are therefore arranged offset from one another in a direction defined by the electrode center line 156.

To enable a high-frequency current to be applied to the electrode segments 150, 151, these are respectively arranged electrically conductively with a high-frequency connection 158 in proximal end regions of the arms 124, 126 adjacent to the finger rings 128, 130. The high-frequency connections 158 can be connected with corresponding connection lines or cables to the high-frequency current generator 18.

In the approach position, owing to the identical configuration of the high-frequency electrodes 142 and 144, electrode segments 150 and 151 of the same or substantially the same size are located opposite each other and face each other. They form an electrode segment pair generally designated by reference numeral 168. The instrument 120 therefore comprises in all 32 electrode segment pairs 168.

The tool elements 138 and 140 also define flat tool element surfaces 170, which are of U-shaped configuration. The electrode segments 150 and 151 do not project over the tool element surface 170.

The instrument 120 of generally forceps-type configuration can also be used to connect parts of tissue. These are held clamped between the tool elements 138, 140 and are then welded or sealed to one another by corresponding application of current to the electrode segments 150, 151. To this end, as described in conjunction with the operation of the instrument 12, current can be applied to the electrode segments 150 sequentially, i.e., in a circulating U-configuration, after application of current to one electrode segment 150, current is applied to the next electrode segment 150 of the adjacent electrode row 152, 154 until current has been applied once to all electrode segments 150, 151. In this way, a two-row connection line for connecting two parts of tissue can be created. Alternatively, in the instrument 120 simultaneous application of current to two or even more electrode segments 150, 151 is also conceivable. Preferably, current is not simultaneously applied to adjacent electrode segments 150, 151, but rather, preferably, at least one, better two or three electrode segments 150, 151 between electrode segments 150, 151 having current applied simultaneously to them remain without current.

The instrument 120 can also optionally comprise a cutting device 160, as represented diagrammatically in FIG. 6. A slot 162 is formed between the electrode sections 146 on the tool elements 138, 140. A cutting element 164 with a cutting edge 166 pointing in the direction towards the slot 162 of the arm 124 is held in the slot 162 on the arm 126 and is optionally movable relative to the tool element 136. Therefore, the tissue held between the tool elements 138 and 140, for example, can already be severed upon closing the arms 124 and 126. Optionally, the cutting element 164 can also be used in a monopolar or bipolar manner. For example, the high-frequency electrode 142 can be used as counter electrode to the cutting element 164 in the case of bipolar use. For monopolar operation, a high-frequency current is merely applied to the cutting element 164 and a neutral electrode placed on the patient's body as counter electrode. In both cases, the cutting element 164 is preferably also electrically conductively connected to a contact of the high-frequency connections 158.

In FIGS. 8 to 11 a variant of the instrument 12 is represented, which differs by the configuration of the second tool element, which is designated in FIGS. 8 to 11 by reference numeral 16'. The tool element 16' assumes, in an operating position in which it can be moved into the approach position described above, the shape of a circular ring. It comprises two circular ring sections 180 and 182, which each extend over an angle of about 180° in relation to the longitudinal axis 54. Free ends of the circular ring sections 180, 182 are only half as wide as the circular ring sections 180, 182 in the remaining region and serve as bearing blocks 184 and 186. The bearing blocks 184 and 186 are each provided with a transverse bore 188 and 190, into which a cylindrical rod 192 is inserted. The bearing blocks 184 lie against the side of the bearing blocks 186 that faces the longitudinal axis 54. The rod 192 is rotationally fixedly secured in the transverse bores 190 of the circular ring section 182. The inner diameter of the transverse bore 188 is of such dimensions that the circular ring section 180 is pivotable relative to the rod 192 about a pivot axis 242 defined thereby and therefore relative to the circular ring section 182.

The two circular ring sections 180 and 182 are each additionally coupled by a bar-shaped link 194 to a holding member 84' which defines a holding member longitudinal axis coinciding with the longitudinal axis 54. In analogy with the holding member 84, the holding member 84' is or can be coupled to the force transmitting member 80, and in this way is movable in the distal and proximal directions relative to the shaft 24. For movable articulation of the links 194 on the holding member 84', the latter is provided in the region of its distal end with a slot 204, which extends transversely to a longitudinal axis defined by the rod 192. In this way, two legs 206 are formed, which are provided with an aligning transverse bore 208, into which a cylindrical bearing pin 210 is rotationally fixedly inserted. The links 194 are provided at their first ends with a receiving bore 212, through which the bearing pin 210 extends, and which has an inner diameter allowing pivotal movement of the links 194 about a pivot axis defined by the bearing pin 210.

On the proximal side of the slot 204 in the holding member 84' there extends further in the proximal direction a longitudinal slot or oblong hole 214, through which the rod 192 passes. In this way, the rod 192 is defined and displaceable parallel to itself in a direction parallel to the longitudinal axis 54. A proximal end of the oblong hole 214 forms a proximal end stop for the rod 192, and a distal end 218 of the oblong hole 214 forms a distal end stop for the rod 192.

An actuating mechanism 222, which comprises a sleeve-shaped force transmitting element 220 whose inner diameter is adapted to the outer diameter of the holding member 84' and is therefore displaceable in the distal and proximal directions on the holding member 84', serves to move the rod 192. Adjacent to its distal end 224, the force transmitting element 220 is provided with a bore 226 through which the rod 192 extends. The rod 192 is rotatable relative to the bore 226. The actuating mechanism 222 can also form part of the actuating mechanism 76 described above. This means that movement of the rod 192, for example, also by pivotal movement of the actuating members 100 relative to one another, is possible. Alternatively, it is conceivable to provide, in analogy with the actuating mechanism 76, a further actuating device which comprises one or two further actuating members, similar to the actuating members 100, in order to specifically bring about relative movement between the force transmitting element 220 and the holding member 84'.

There are arranged parallel to each other on upper sides of the circular ring sections 180 and 182 two bearing blocks 228, which are provided with bores 230 parallel to the transverse bore 208. A further free end of the links 194 is pivotably mounted, in each case, between the bearing blocks 228 on the bearing shaft 200 inserted in the bores 230. The described arrangement of the links 194, which may also be referred to as articulation members, ensures that they engage at one end the second tool element 16' at an engagement or articulation point which is spaced at a distance from the pivot axis 242.

Figure 9:
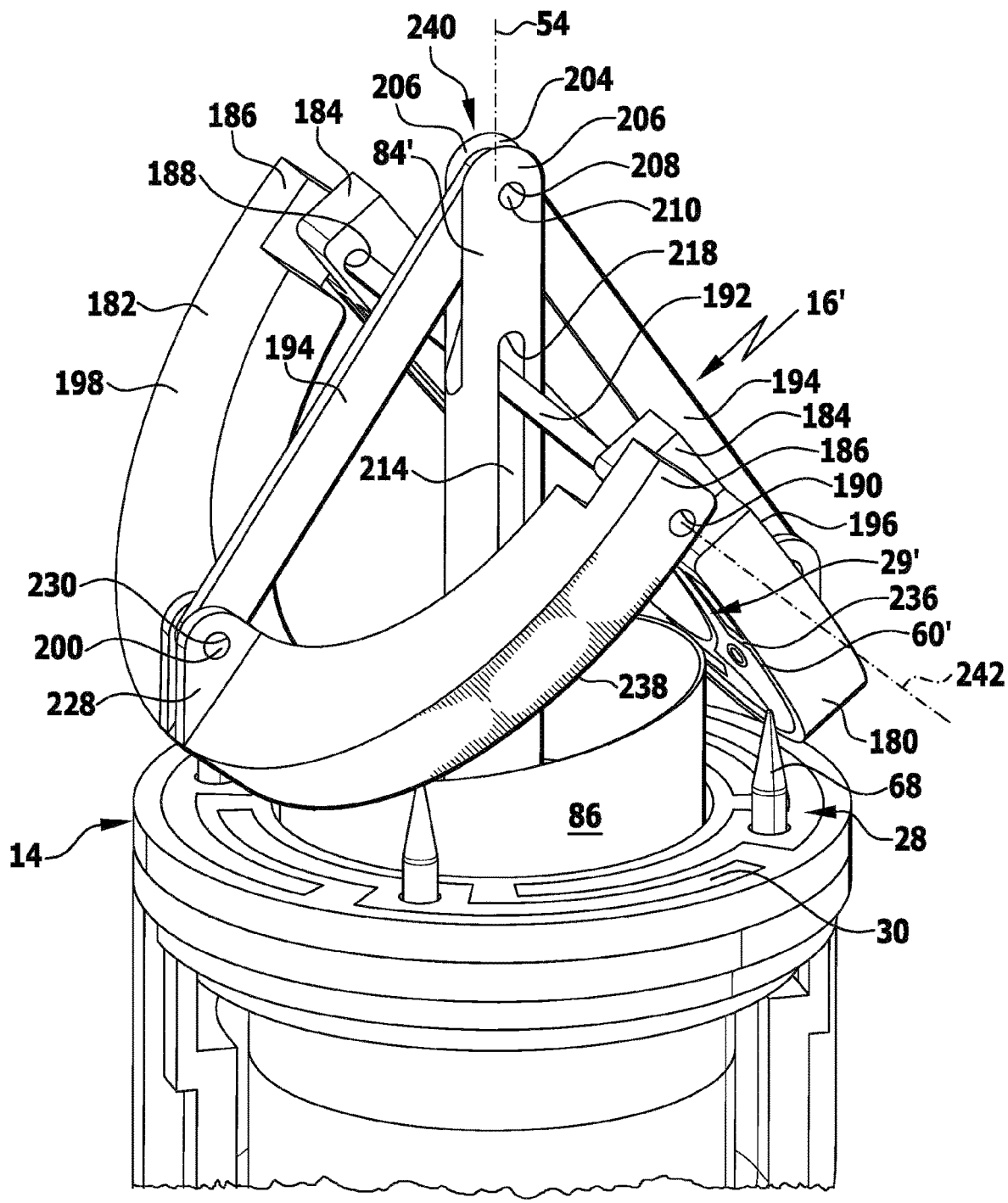
FIG. 9 shows a view corresponding to FIG. 8 of the instrument represented therein with the second tool element partly folded down.
Figure 10:
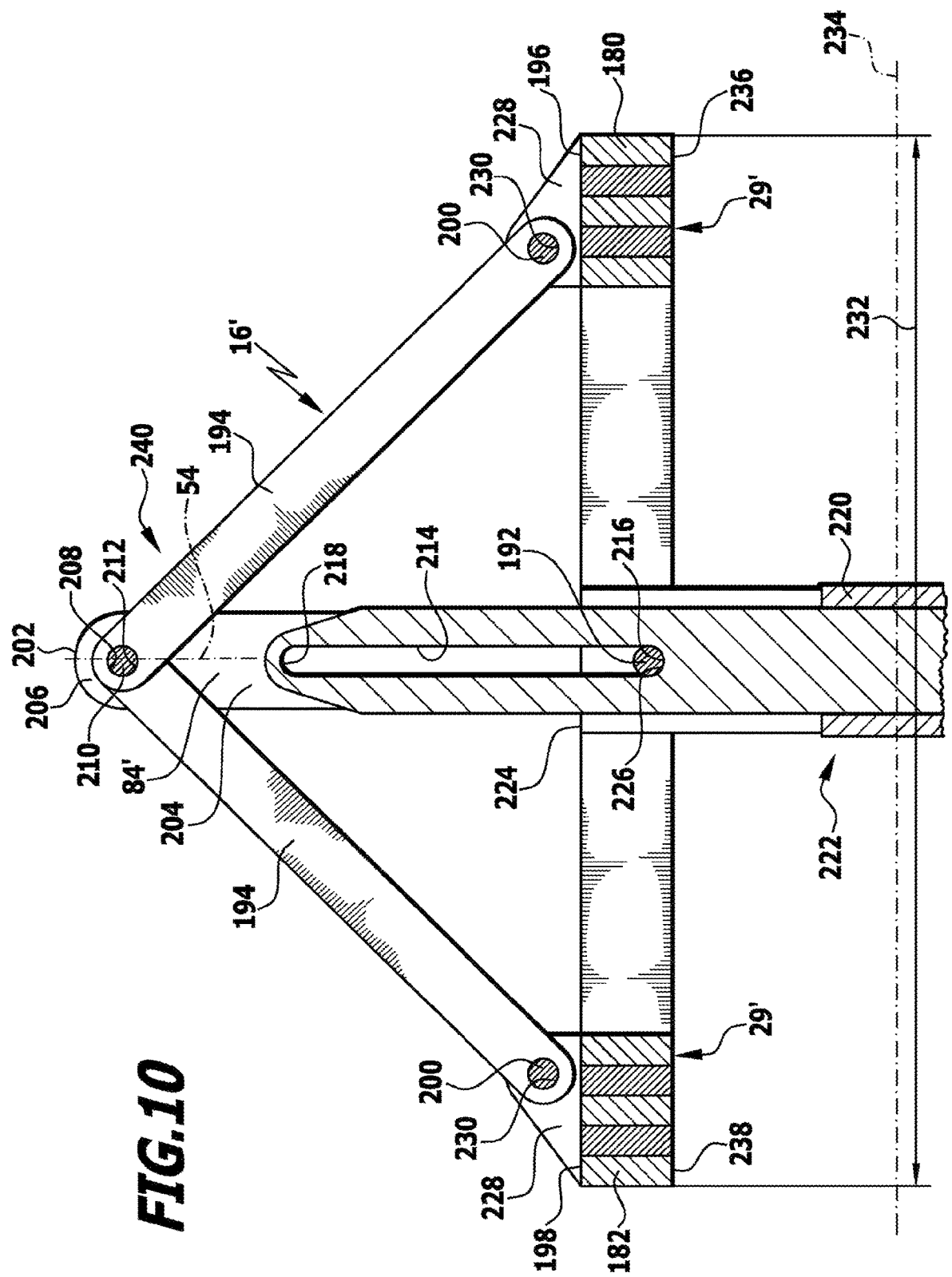
FIG. 10 shows a sectional view taken along line 10-10 in FIG. 8.
Figure 11:
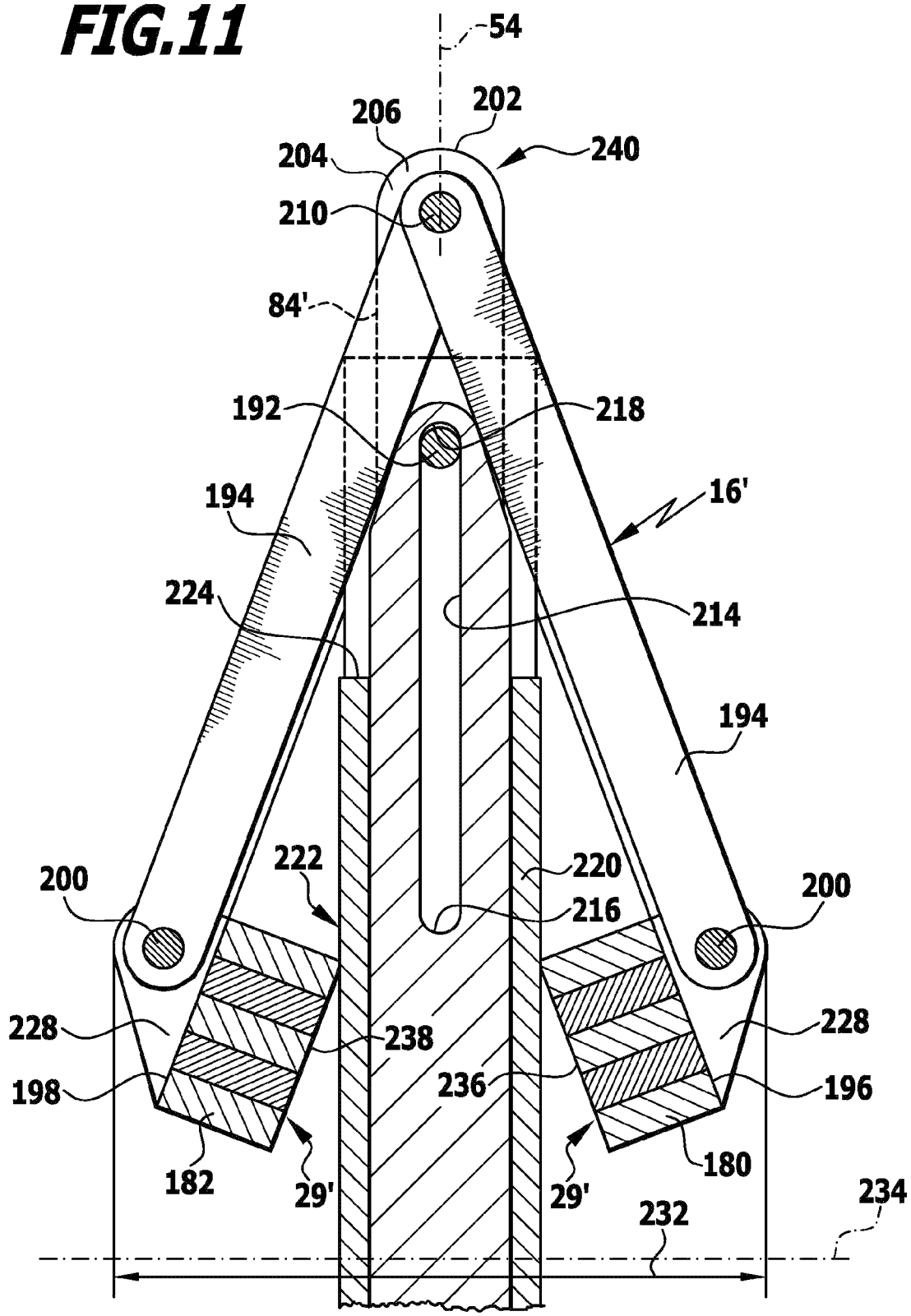
FIG. 11 shows a diagrammatic sectional view similar to FIG. 10 of the second tool element collapsed in a position as represented in FIG. 9.
Figure 12:
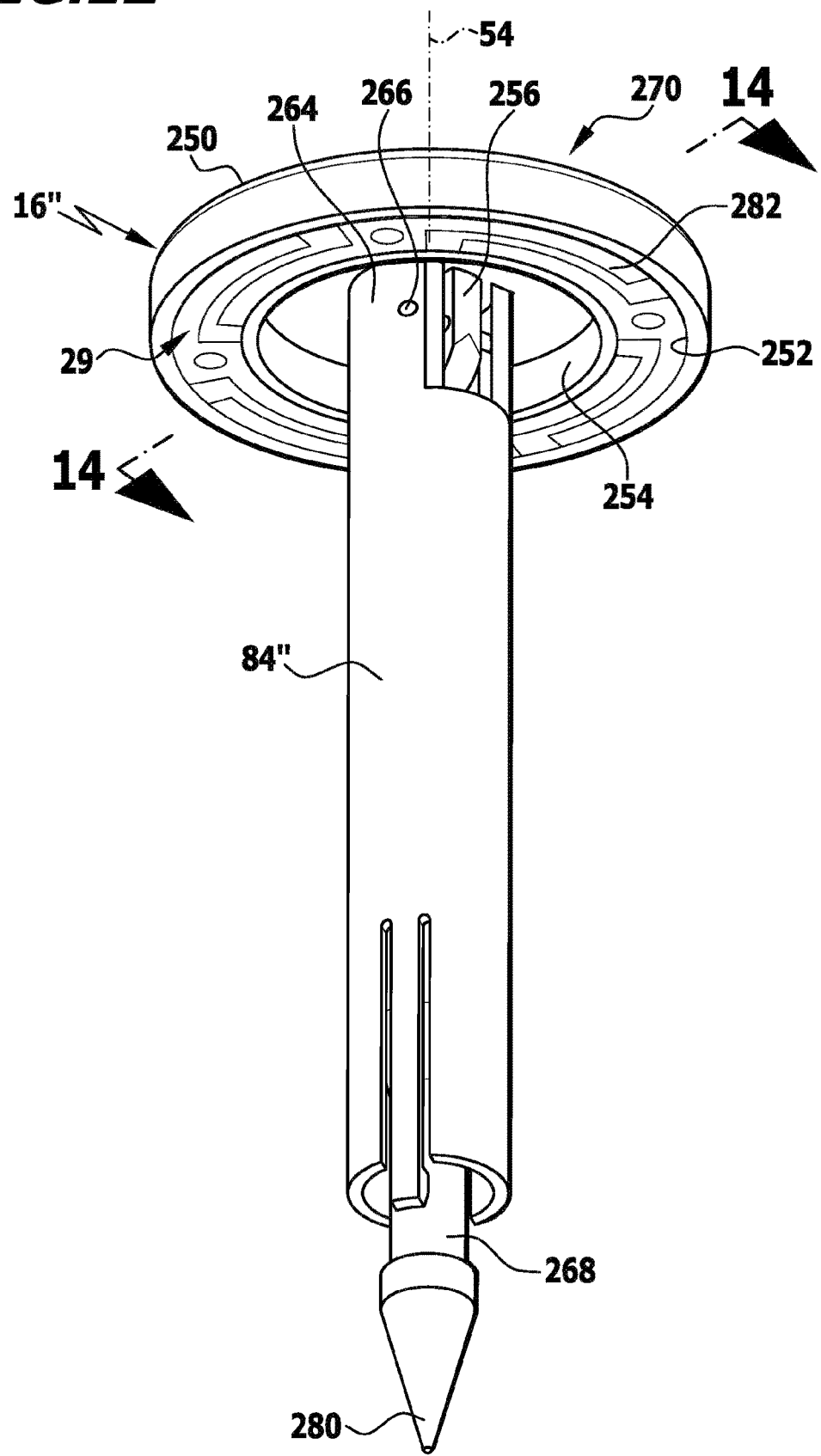
FIG. 12 shows an alternative embodiment of a second tool element in perspective diagrammatic representation.
Figure 13:
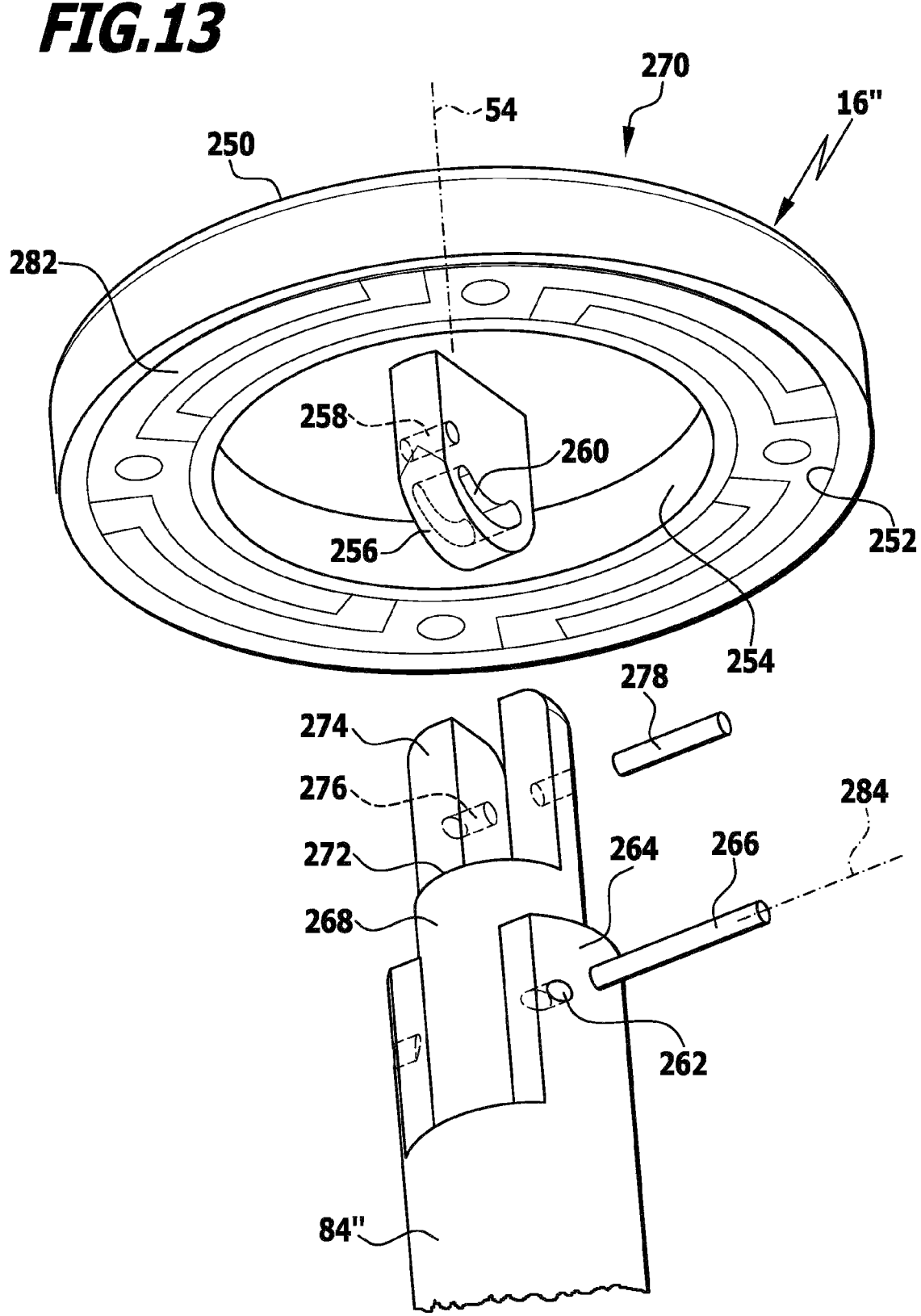
FIG. 13 shows an exploded representation of part of the second tool element represented in FIG. 12.
Figure 14:
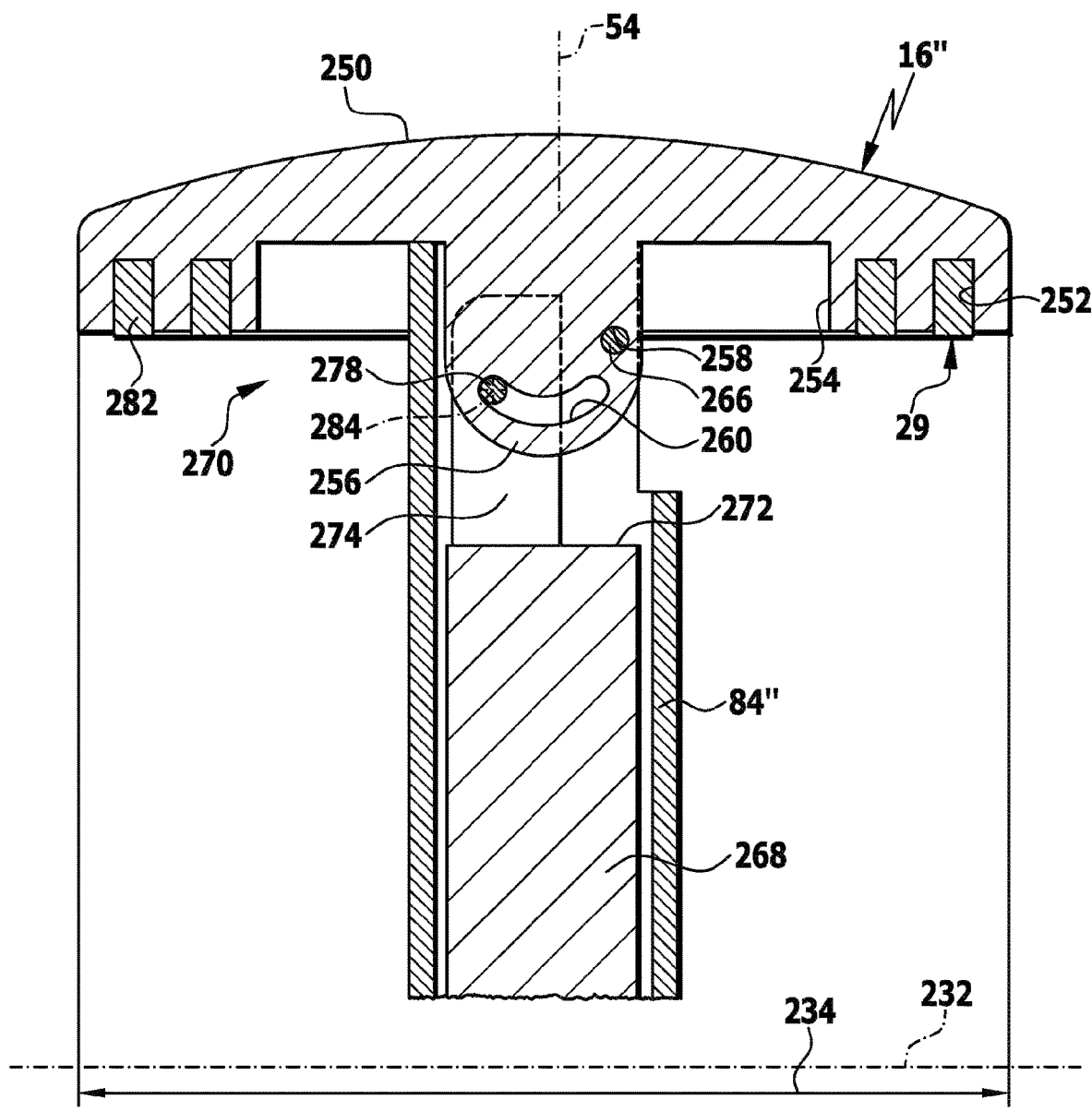
FIG. 14 shows a sectional view taken along line 14-14 in FIG. 12.
Figure 15:
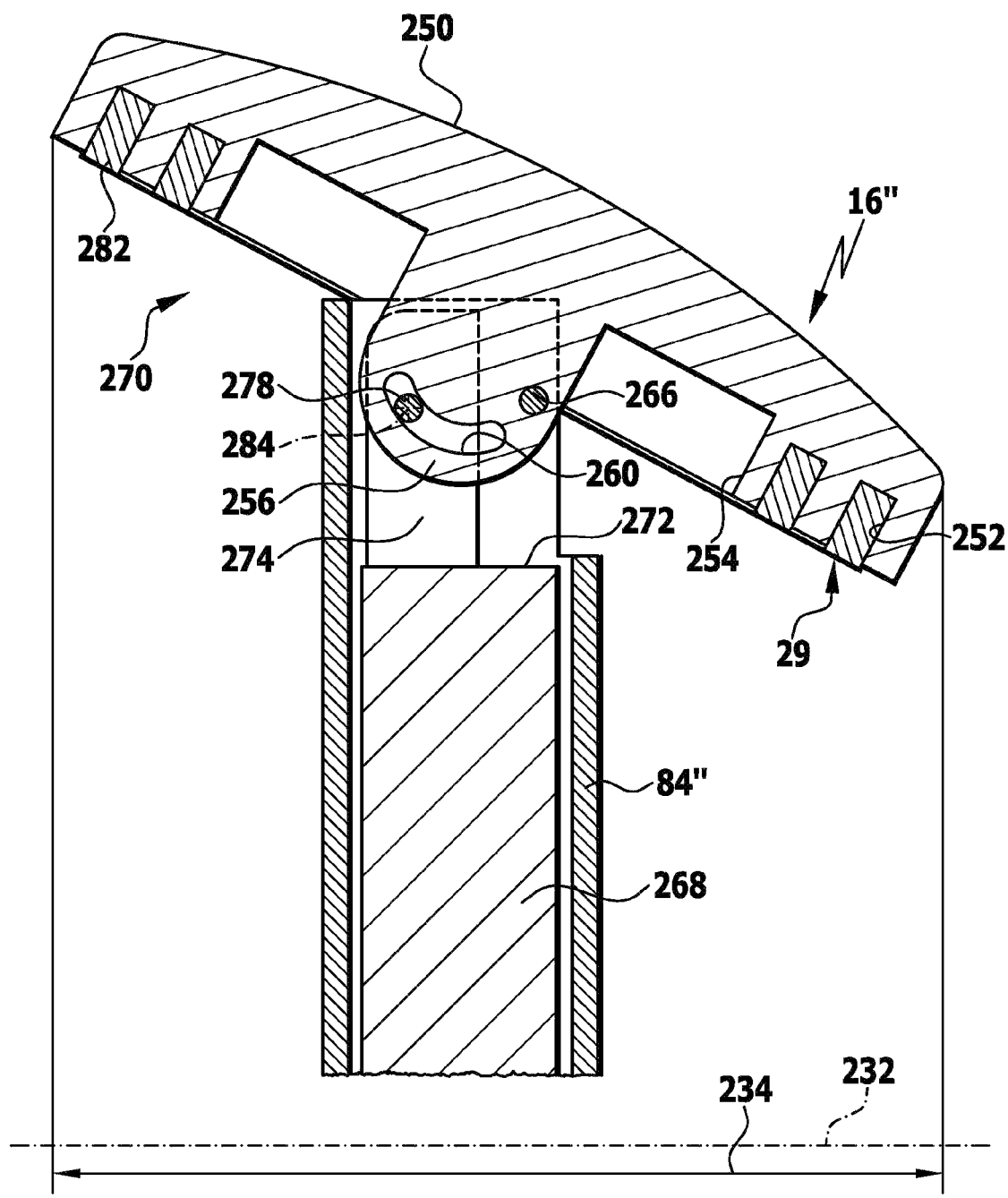
FIG. 15 shows a schematic sectional view in analogy with FIG. 14 of the embodiment represented therein with the second tool element partly folded down.
Figure 16:
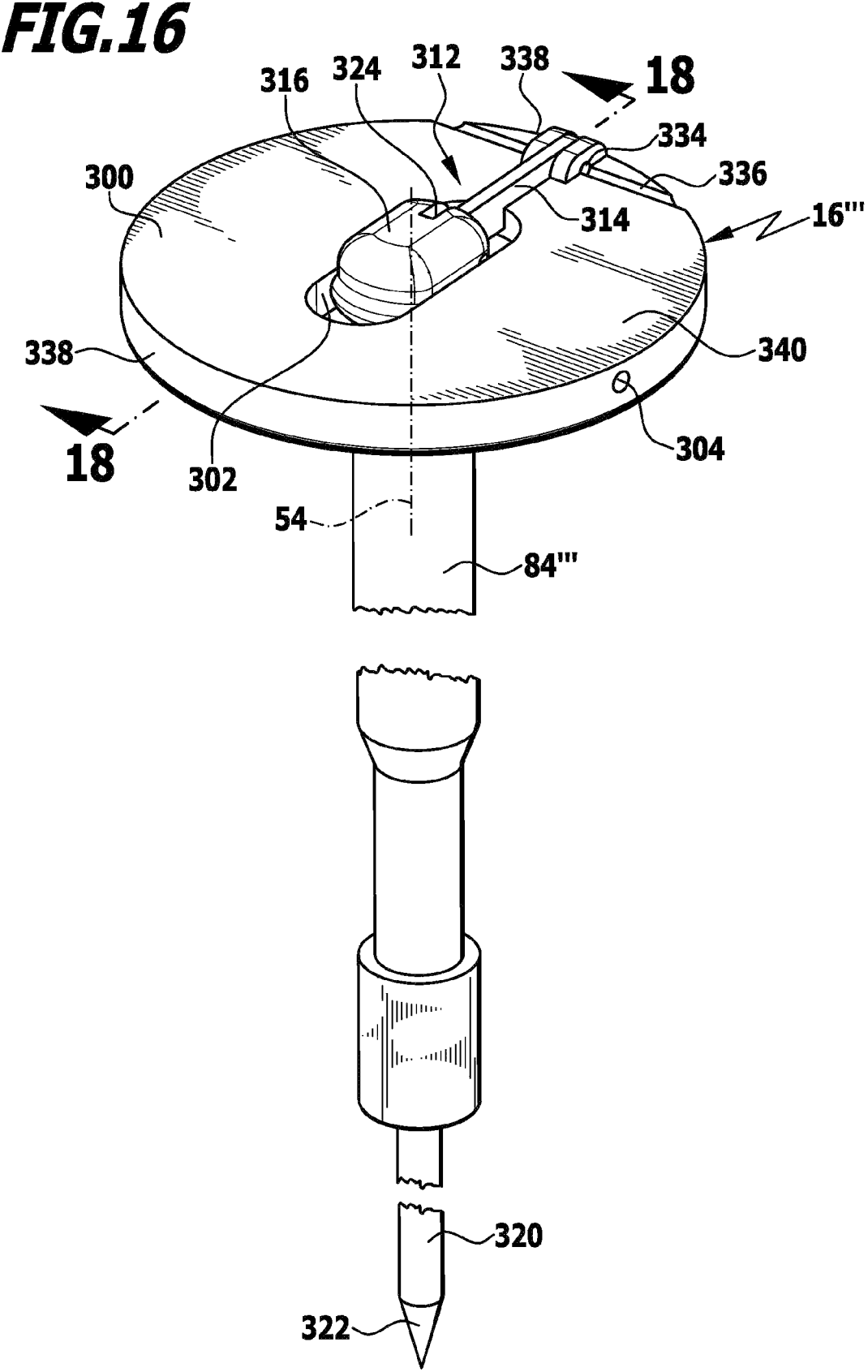
FIG. 16 shows a perspective diagrammatic representation similar to FIG. 12 of a further embodiment of a second tool element.
Figure 17:
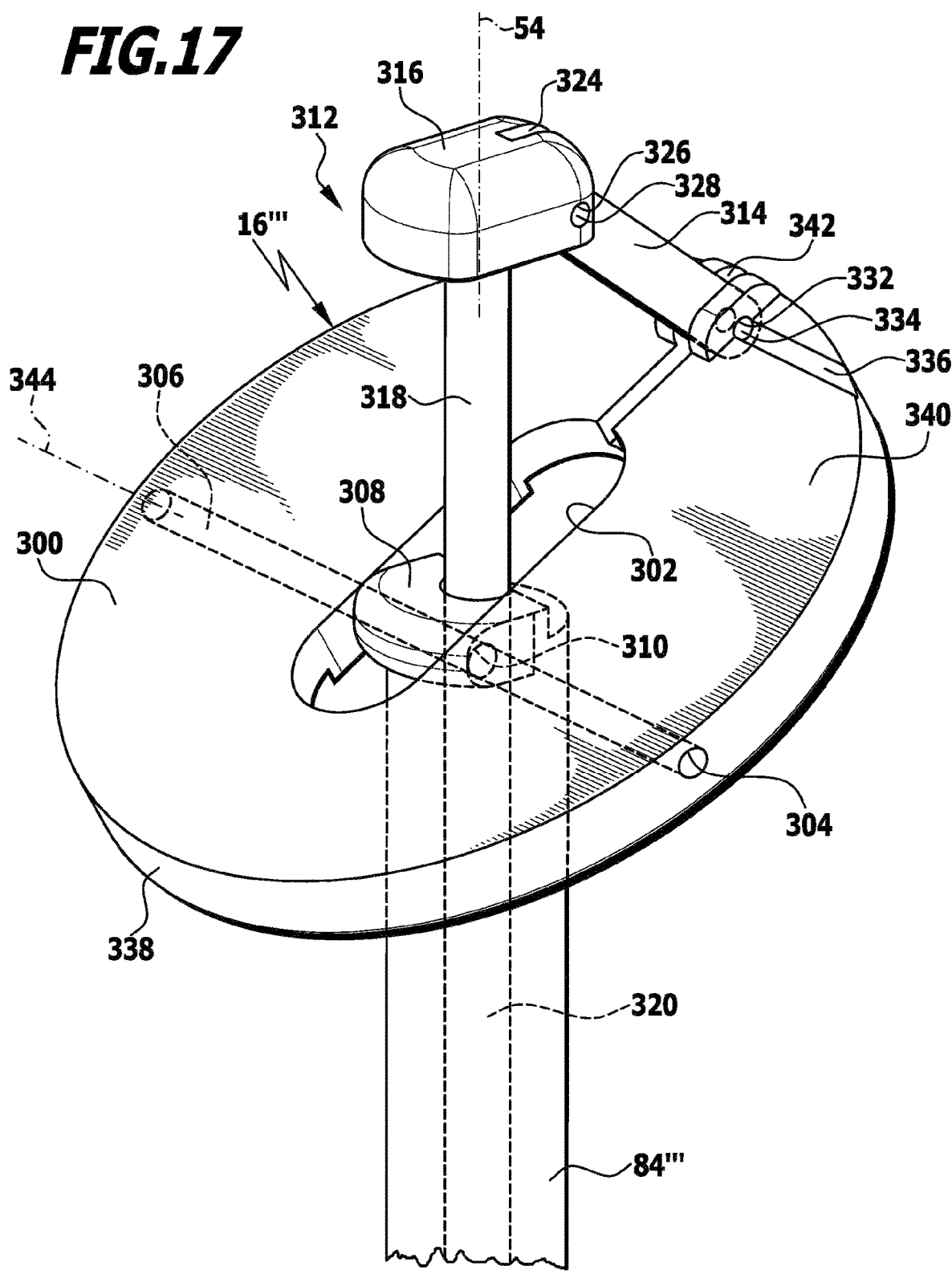
FIG. 17 shows an enlarged representation of the second tool element from FIG. 16 in a partly inclined position.
Figure 18:
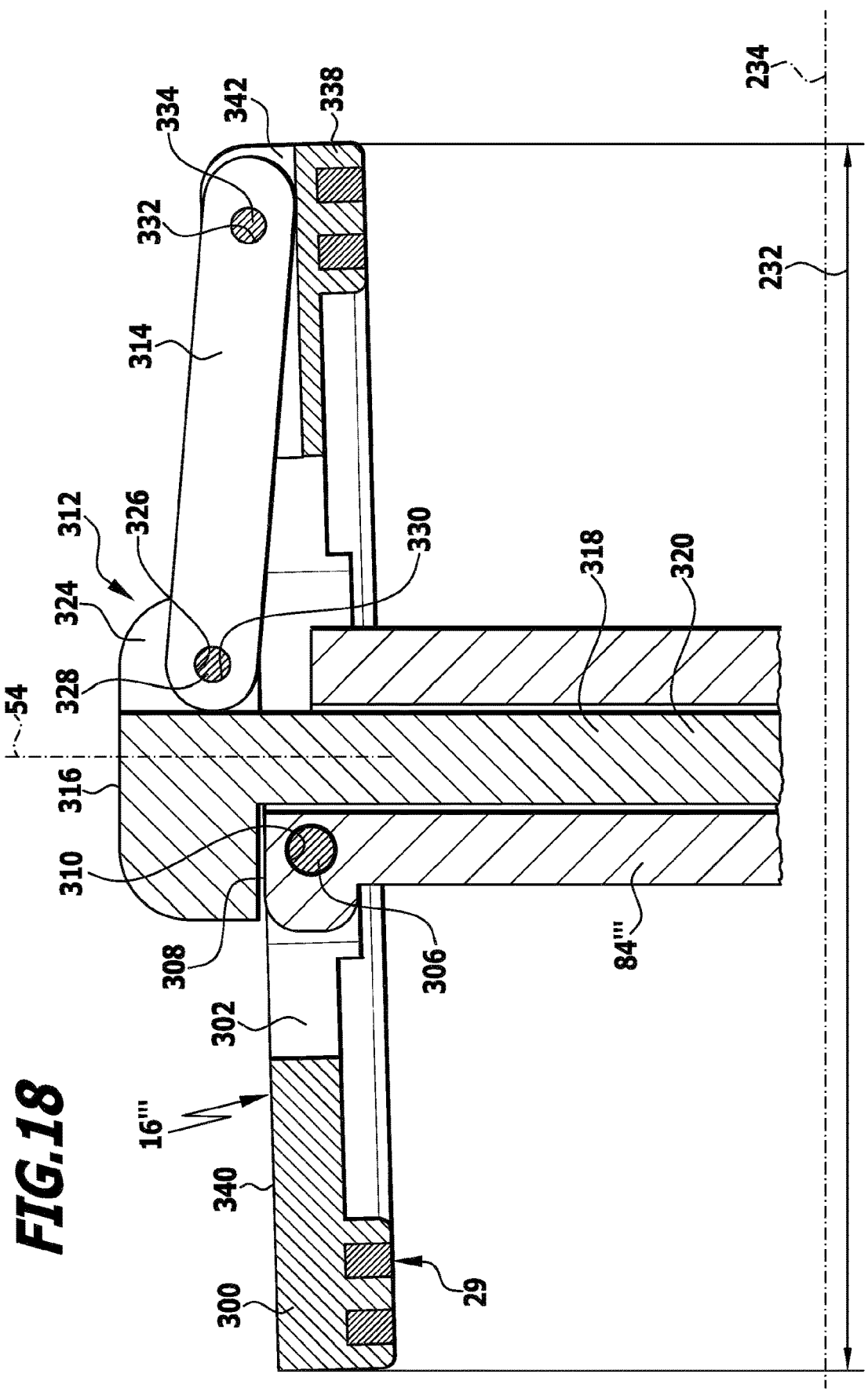
FIG. 18 shows a sectional view taken along line 18-18 in FIG. 16.

By means of the actuating mechanism 222, the second tool element 16' can be moved from the operating position mentioned above, which is diagrammatically shown in FIGS. 8 and 10, into the removal position, which is represented by way of example in FIG. 11. FIG. 9 represents diagrammatically an intermediate position, i.e., a position between the operating position and the removal position. As will be readily apparent from comparison of the two FIGS. 10 and 11, a surface area of a perpendicular projection of the second tool element 16' onto a projection plane 234 extending perpendicularly to the longitudinal axis 54, i.e., to the shaft direction in the region of the second tool element 16', is smaller in the removal position than in the operating position. This is achieved by movement of the sleeve-shaped force transmitting element 220, starting from the operating position in which the rod 192 strikes the proximal end 216, and undersides 236 and 238 of the circular ring sections 180 and 182 extend parallel to the projection plane 234. When the force transmitting element 220 is moved in the distal direction, the rod 192 is forcibly guided in the distal direction in the oblong hole 214. Owing to the articulated connection of the circular ring sections 180 and 182 relative to each other and to the holding member 84' by the two links 194, the circular ring sections 180 and 182 pivot about the pivot axis 242 in the direction towards the longitudinal axis 54. In this way, the second tool element 16' is folded together or collapsed. By the articulated arrangement of the circular ring sections 180 and 182 by means of the links 194 a folding mechanism 240 is thus formed for transferring the second tool element 16' from the operating position to the removal position.

So far, the configuration of the undersides 236 and 238 of the second tool element has not been discussed. These can either comprise a single, substantially continuous ring electrode which forms a single counter electrode to the high-frequency electrode 28 of the first tool element 14. Or, alternatively, there can also be formed on the undersides 236 and 238, in analogy with the high-frequency electrode 29, a high-frequency electrode with two or more electrode segments 31, preferably corresponding to the high-frequency electrode 29. This then allows connection of parts of tissue 116 in the manner described above in the operating position.

After the connecting of the parts of tissue, the folding mechanism 240 can then be actuated, for example, by corresponding actuation of the described actuating mechanism 222, whereby the holding member 84' is moved in the distal direction. If the force transmitting element 220 is, for example, immovably arranged relative to the shaft 24, then the second tool element 16' can be automatically collapsed upon movement in the distal direction of the force transmitting member 80. Owing to the significantly reduced space requirement in the removal position, the second tool element can be guided, during removal of the instrument 12, through a connection site formed by connecting the parts of tissue 116, more particularly, without expanding the connection site, which is much more gentle than passing the second tool element through the connection site in the operating position.

It is self-evident that electrically conductive connections from the electrode 29 to the high-frequency connecting contacts 50 can be led, for example, via the links 94 and the holding member 84' to the high-frequency connecting contacts 50 in the proximal end region of the shaft 24.

A further variant of a second tool element is generally designated by reference numeral 16" in FIGS. 12 to 15. It replaces, for example, the above-described tool elements 16 and 16' of the instrument 12.

The second tool element 16" is substantially plate-shaped with a slightly convexly curved outer side 250 pointing in the distal direction.

A ring groove 252 which is open and points in the proximal direction is formed on an underside of the second tool element 16". Formed at the center is a substantially circular depression 254 in which a substantially parallelepipedal bearing projection 256 is arranged. The bearing projection 256 is formed coaxially with the longitudinal axis 54 and protrudes in the proximal direction from the underside of the second tool element 16". The bearing projection 256 is provided with a transverse bore 258 which is skew in relation to the longitudinal axis 54. There is also formed on the bearing projection 256 a curved guide slot 260, which is of convexly curved configuration pointing in the proximal direction. A proximal end of the bearing projection 256 has a rounded-off outer contour.

The second tool element 16" is mounted for pivotal movement on a sleeve-shaped holding member 84". For this purpose, the holding member 84" is provided with a transverse bore 262, which extends through a wall 264 of the holding member 84" at two points. Rotationally fixedly inserted in the transverse bore 262 is a bearing pin 266. It simultaneously extends through the transverse bore 258 in such a way that the bearing projection 256 is pivotable about a pivot axis 284 defined by the bearing pin 266. To enable actuation of a folding mechanism 270 also provided in the second tool element 16", a force transmitting element 268 is provided, which is of substantially rod-shaped configuration and extends through the holding member 84" coaxially with the longitudinal axis 54. Arranged so as to project from a distal end surface 272 of the force transmitting element 268 parallel to each other and pointing in the distal direction are two bearing legs 274, through each of which an aligning bore 276 extends. Rotationally fixedly inserted in the bores 276 is a further bearing pin 278, which is oriented parallel to the bearing pin 266. An outer diameter of the bearing pin 278 is of such dimensions that it can extend through the guide slot 260 and be moved relative thereto.

A proximal end 280 of the force transmitting element 268 can preferably be coupled to the force transmitting member 80, so that as a result of movement of the latter, the second tool element 16" can also be moved.

Inserted in the ring groove 252 is a ring-shaped electrode element 282, which preferably comprises a high-frequency electrode 29 in the above-described form, which, for reasons of clarity, is not shown in detail in FIGS. 12 to 15. Alternatively, a simple, continuous ring electrode can also be formed on the electrode element 282.

To transfer the second tool element 16" from the operating position to the removal position, the force transmitting element 268 is moved in the distal direction. Owing to the specially curved guide slot 260, the bearing pin 278 is forcibly guided therein and therefore brings about a forcibly guided pivoting of the second tool element 16" about the pivot axis 284. Essentially, the second tool element 16" can thus be pivoted through almost 90°, so that in this variant of the tool element 16", too, a perpendicular projection 232 thereof onto the projection plane 234 is smaller in the removal position than in the operating position, as represented diagrammatically in FIGS. 14 and 15. In this way, an overstretching of the connection site between the parts of tissue 116 connected to one another is avoided in the removal position when removing the instrument 12.

A further embodiment of a second tool element generally designated by reference numeral 16''' is shown in FIGS. 16 to 19. It can be used in the instrument 12 instead of the previously described second tool elements 16, 16' and 16''.

The second tool element 16''' is substantially plate-shaped and comprises a disc 300. This is provided at its center with an elongated oval slot 302 extending transversely. A bore 304 extends through the disc 300 offset latterly somewhat from its center point, which lies in the region of the slot 302. Rotationally fixedly inserted in the bore 304 is a bearing pin 306, which also extends through the slot 302. A distal end of a holding member 84''', which is of sleeve-shaped configuration, projects into the region of the slot 302. Proximally from its end 308, the holding member 84''' is provided with a bore 310 whose inner diameter is so adapted to the outer diameter of the bearing pin 306 that the bearing pin 306 is rotatable relative to the bore 310 therein. This then enables, all in all, a pivoting of the disc 300 about a longitudinal axis defined by the bearing pin 306.

A folding mechanism 312, which couples the disc 300 via a link 314 articulatedly to a distal end 316 of a force transmitting element 318, serves for forcibly actuated pivoting of the disc 300. The force transmitting element 318 has an elongate, rod-shaped section 320 whose proximal end 322 can be coupled to the force transmitting member 80. The end 316 is thickened in the shape of a head in relation to the section 320 and is of almost parallelepipedal shape. A slot 324 open at the side is formed at one side thereof. A transverse bore 326 is also provided, which extends transversely through the slot 324. Rotationally fixedly inserted in the transverse bore 326 is a bearing pin 328. The rod-shaped link 314 is also provided with a bore 330 and is mounted for pivotal movement on the bearing pin 328. A further bore 332 is provided adjacent to an opposite end of the link 314. It serves to mount the link 314 on a further bearing pin 334. This is inserted in a further bore 336 of the disc 300. The bore 336 is oriented parallel to the bore 304 and arranged outside the slot 302 adjacent to an edge 338 of the disc 300, more particularly, opposite the bore 304 in relation to the longitudinal axis 54. Formed on an upper side 340 of the disc 300, starting from the edge 338 is a groove 342 into which the end of the link 314 enters with its bore 332. In this way, the link 314 is articulately mounted on the bearing pin 334. With one end, the link 314 thus engages the second tool element 16''' at an engagement or articulation point which is spaced at a distance from a pivot axis 344 which is defined by the longitudinal axis of the bearing pin 306.

The folding mechanism 312 is actuated by the force transmitting element 318 being moved in the distal direction. This has the consequence that the link 314 is bent relative to the disc 300. The further the force transmitting member 318 is moved in the distal direction, the further the link 314 pulls the region of the disc 300 on which the groove 342 is provided in the distal direction. In an extreme position, the disc 300 is then aligned almost parallel to the longitudinal axis 54. All in all, it is therefore also possible with the second tool element 16''' to attain a removal position in which a perpendicular projection 232 thereof onto the projection plane 234 extending perpendicularly to the longitudinal axis 54 is smaller than in the operating position.

A high-frequency electrode 29 in a form as described above in the second tool element 16 can also be arranged or formed on the second tool element 16'''. Alternatively, it is also conceivable to provide a self-contained, ring-shaped electrode which is not divided up into electrode segments. Similarly to how the second tool element 16'' comprises the electrode element 282, electrode elements, for example, in the form of the electrode element 282 or else the electrode element 52 can also be provided in the second tool elements 16' and 16'''.

As mentioned above in conjunction with the second tool element 16', the high-frequency electrodes provided on the second tool elements 16'' and 16'' can be connected in the conventional manner to the high-frequency connecting contacts 50 by providing corresponding electrically conductive connections on the instrument 12.

All of the above-described first and second tool elements 14, 16, 16', 16'', 16''' and 138 and 140 are preferably comprised of either electrically conductive or electrically insulating components. Components are also conceivable, which are partly electrically conductive and partly electrically insulating. The components themselves can, in particular, be produced completely from electrically conductive or electrically insulating materials, and the electrically insulating components can also be produced from an electrically conductive material which, in particular, is provided with an electrically insulating outer sheath or coating. As electrically insulating or non-conductive materials, in particular, plastics can be used, which still have sufficient stability at the temperatures occurring when the surgical system 10 is in use. For example, both thermoplastics and thermosetting plastics are suitable. Alternatively, ceramic material can also be used as insulating material. In particular, the components of the tool elements 14, 16, 16', 16'', 16''' and 138 and 140 can be made from a ceramic material. Use of a ceramic material has the advantage, in particular, over many plastics that it still has sufficient stability at very high temperatures. The high-frequency electrodes 28 and 29 are preferably made from a metal or a metal alloy. Alternatively, the use of electrically conductive ceramic materials for formation of the high-frequency electrodes 28 and 29 is also conceivable, provided they meet the requirements for use of high-frequency current.

The tool elements 14, 16, 16', 16'', 16''' and 138 and 140 can, for example, be produced as described hereinbelow. The individual parts, components or constituents of the tool elements 14, 16, 16', 16'', 16''' and 138 and 140 can, in particular, be produced separately and subsequently fitted together, for example, adhesively. Alternatively, it is, for example, also possible to place the electrically conductive parts of the high-frequency electrodes 28 and 29 as inserts in a plastic injection molding tool and to injection-mold these with a plastic material. As mentioned above, the electrodes can be made from a metal or an electrically conductive ceramic material. In the case of segmentation of the high-frequency electrodes 28 and 29 as described above, for example, a corresponding number of electrically conductive electrode segments made from a metal or a metal alloy or an electrically conductive ceramic material must then be placed in the plastic injection molding tool before injection-molding with a suitable plastic material.

In the case of purely ceramic construction of the tool elements 14, 16, 16', 16'', 16''' and 138 and 140, in particular, a ceramic powder injection molding method can be used, for example, the so-called "2C-CIM" technology, a two-component microceramic powder injection molding method. Herein two different ceramics are injected in an injection molding process, which form the electrically conductive and electrically insulating parts in the finished tool elements 14, 16, 16', 16'', 16''' and 138 and 140. After the injection, the two different ceramics are sintered together. These can be, for example, an $Al_2O_3$ ceramic and a mixed ceramic made of $Al_2O_3$ and TiN.

What is claimed is:

1. Surgical system for connecting tubular parts of body tissue, for end-to-end, side-to-end or side-to-side anastomosis, comprising:
 a surgical instrument comprising:
  a first ring-shaped or plate-shaped tool element and a second ring-shaped or plate-shaped tool element movable relative to each other, each of which forms a ring-shaped, self-contained high-frequency electrode element, at least one of the high-frequency electrode elements comprising more than two arc-shaped strip electrodes electrically insulated from each other which extend in a circumferential direction, the high-frequency electrode elements, in an approach position of the tool elements, defining a minimum distance from each other, lying opposite each other and facing each other, and
  a shaft at a distal end of which at least the first tool element is arranged or formed,
 wherein:
  portions of adjacent arc-shaped strip electrodes of the more than two arc-shaped strip electrodes overlap one another,
  a sum of lengths of the more than two arc-shaped strip electrodes exceeds a length of the at least one high-frequency electrode element, and
  the second tool element is adapted to be moved from an operating position, in which it is adapted for movement into the approach position, into a removal position and/or vice versa, such that a surface area of a perpendicular projection of the second tool element onto a projection plane extending perpendicularly to a shaft direction in a region of the second tool element being smaller in the removal position than in the operating position.

2. Surgical system in accordance with claim 1, wherein the second tool element is mounted for movement on a holding member.

3. Surgical system in accordance with claim 2, wherein the second tool element is mounted for pivotal movement about a pivot axis which extends perpendicularly to a holding member longitudinal axis defined by the holding member.

4. Surgical system in accordance with claim 2, further comprising a folding mechanism for transferring the second tool element from the operating position into the removal position.

5. Surgical system in accordance with claim 4, wherein the folding mechanism comprises a force transmitting element for transmitting an actuating force onto the second tool element to transfer the second tool element from the operating position into the removal position and/or vice versa.

6. Surgical system in accordance with claim 5, wherein the force transmitting element and the holding member are configured for at least one of displacement, rotation, and screwing relative to each other.

7. Surgical system in accordance with claim 5, further comprising an actuating mechanism coupled with at least one of the folding mechanism, the force transmitting element, and the holding member for at least one of actuating the folding mechanism and moving the force transmitting element and/or the holding member relative to the shaft.

8. Surgical system in accordance with claim 5, wherein the second tool element and the force transmitting element are articulatedly coupled to each other by at least one articulation member.

9. Surgical system in accordance with claim 1, wherein the second tool element is of two-part or multi-part configuration.

10. Surgical system in accordance with claim 1, wherein the second tool element comprises at least two tool element parts which are movable relative to each other during a transition from the operating position to the removal position.

11. Surgical system in accordance with claim 1, wherein the electrode element of the second tool element is movable in the shaft direction and movable in a direction towards and away from the first tool element.

12. Surgical system in accordance with claim 1, wherein the instrument further comprises an actuating device for moving the tool elements relative to each other.

13. Surgical system for connecting tubular parts of body tissue, for end-to-end, side-to-end or side-to-side anastomosis, comprising:
 a surgical instrument comprising:
  a first ring-shaped or plate-shaped tool element and a second ring-shaped or plate-shaped tool element movable relative to each other, each of which forms a ring-shaped, self-contained high-frequency electrode element, at least one of the high-frequency electrode elements comprising a plurality of arc-shaped electrode segments electrically insulated from each other which extend in a circumferential direction, the high-frequency electrode elements, in an approach position of the tool elements, defining a minimum distance from each other, lying opposite each other and facing each other, and
  a shaft at a distal end of which at least the first tool element is arranged or formed, wherein:
 portions of the arc-shaped electrode segments overlap one another,
 the electrode segments define two electrode rows;
 each of the electrode rows comprises part of each electrode segment;
 each of the electrode segments comprises a first electrode segment section forming part of the first electrode row, a second electrode segment section forming part of the second electrode row, and a connecting contact arranged in a connection region between the first and second electrode segment sections; and
 the second tool element is adapted to be moved from an operating position, in which it is adapted for movement into the approach position, into a removal position and/or vice versa, such that a surface area of a perpendicular projection of the second tool element onto a projection plane extending perpendicularly to a shaft direction in a region of the second tool element being smaller in the removal position than in the operating position.

* * * * *